United States Patent [19]

Fujimiya et al.

[11] Patent Number: 5,190,632
[45] Date of Patent: Mar. 2, 1993

[54] MULTI-COLORED ELECTROPHORESIS PATTERN READING SYSTEM

[75] Inventors: Hitoshi Fujimiya; Hisanori Nasu, both of Yokohama, Japan

[73] Assignee: Hitachi Software Engineering Co., Ltd., Yokohama, Japan

[21] Appl. No.: 854,872

[22] Filed: Mar. 20, 1992

[30] Foreign Application Priority Data

Mar. 22, 1991 [JP] Japan .................. 3-059175

[51] Int. Cl.⁵ .............. G01N 21/84; G01N 27/26; G01N 27/447; B01D 57/02
[52] U.S. Cl. .................. 204/299 R; 204/182.8; 356/344
[58] Field of Search ........... 204/299 R, 182.8; 356/344

[56] References Cited

U.S. PATENT DOCUMENTS

| | | | |
|---|---|---|---|
| 4,675,059 | 6/1987 | Mei | 149/43 |
| 4,881,812 | 11/1989 | Ohkubo et al. | 356/344 |
| 4,930,893 | 5/1990 | Manian | 356/344 |
| 5,069,769 | 12/1991 | Fujimiya et al. | 204/182.8 |
| 5,100,529 | 3/1992 | Fujii | 204/299 R |

FOREIGN PATENT DOCUMENTS

| | | | |
|---|---|---|---|
| 63-263458 | 10/1988 | Japan | 204/299 R |
| 1-148946 | 6/1989 | Japan | 356/344 |
| 2-203255 | 8/1990 | Japan | 356/344 |

Primary Examiner—John Niebling
Assistant Examiner—John S. Starsiak, Jr.
Attorney, Agent, or Firm—Fay, Sharpe, Beall, Fagan, Minnich & McKee

[57] ABSTRACT

The multi-colored electrophoresis pattern reading system compares the patterns of electrophoresis without a warp to be caused upon electrophoresis by reading the patterns of electrophoresis which is carried out concurrently for plural samples and by labelling the samples with fluorescent substances having different fluorescent wavelengths. The patterns of electrophoresis are read by allowing fluorescence to emit from the plural samples. In reading the fluorescent patterns, optical signals are received by the light receiving section and then the fluorescence having a predetermined wavelength is separated by the fluorescent-wavelength separating section from the optical signals with the aid of an optical filter capable of controlling an angle of incidence relative to the optical axis of the optical filter. The optical signals passed through the fluorescent-wavelength separating section is then subjected to opto-electrical conversion into electric signals which in turn are subjected to signal processing, thereby converting the electric signals into a desired form of data representation.

7 Claims, 13 Drawing Sheets

MULTI-COLORED ELECTROPHORESIS PATTERN READING SYSTEM

BACKGROUND OF THE INVENTION

The present invention relates to a multi-colored electrophoresis pattern reading system and, more particularly, to a multi-colored electrophoresis pattern reading system appropriate for the comparison of a plurality of patterns of electrophoresis by labelling each of samples with fluorescent pigments having different fluorescent wavelengths, subjecting the samples to electrophoresis simultaneously, and reading the resulting patterns of electrophoresis.

Generally, electrophoresis analysis method using samples labeled with a radioactive isotope has been employed for analyzing the sequences of various genes, including diagnosis of diseases deriving from genes, the structures of proteins such as amino acids, etc. The electrophoresis analysis method is a method for analyzing samples by labelling or replacing fragments of a sample with or by a radioactive isotope, subjecting the fragments of the sample to electrophoresis with a gel, and analyzing a pattern of distribution of the fragments of the sample developed by means of electrophoresis.

Description will now be made of the diagnosis of hereditary diseases as an example for reading and analyzing patterns of electrophoresis. The human gene DNA consists of pairs of bases of approximately $3 \times 10^9$ and the sequences of the bases are generally constant among the human beings, although there is a deviation in the sequences of the bases among individuals. This deviation is called a polymorphism of the DNA. The polymorphism of the DNA is seen in the non-hereditary region as well as in the hereditary region and the polymorphism of the DNA appears in many occasions as a polymorphism of proteins that is a phenotype of the polymorphism of the DNA. A variety of variations as seen among the human beings, such as the blood types, histocompatible antigens, the difference of skin and hair colors among peoples, etc. are based on the polymorphism of the DNA. The polymorphism of the DNA has been created on the basis of variations that have been accumulated in the DNA of the genocytes of the human groups up to the present time from the time when the human beings were developed as an individual biological species in the course of the evolution of the human beings. When such a variation exists in the site that has the function of significance in terms of the existence as an individual person and when a nosogenic phenotype resulting from the variation occurs as a pathologic state, the pathologic state is called a hereditary disease. It is said that there are currently more than 3,000 kinds of hereditary diseases in the human group.

The nosogenesis of the hereditary disease is an abnormality appeared on the DNA sequence. However, it is recognized for the first time as a disease in several stages ranging from a DNA through a mRNA and proteins to pathogenic phenotype. The diagnosis as a disease is conducted usually in the last stage and the diagnosis can be implemented at the DNA level or at the protein level if the disease would occur simply in the course of the several stages as described hereinabove.

The basic technique for the diagnosis of a DNA is called Southern plotting that basically consists of six steps:

Step 1: Extraction of a DNA as a sample;
Step 2 Fragmentation of the DNA with restricting enzymes;
Step 3: Fractionation of DNA fragments by molecular weights through gel electrophoresis;
Step 4: Migration of DNA fractions to filter;
Step 5: Hybridization of the DNA fractions with a probe DNA (obtained by labelling a DNA having a hemeomorphous sequence of the gene to be detected); and
Step 6: Detection of the hybrid by autoradiography.

For the diagnosis of the hereditary diseases, the DNA extracted from any organ is employed and the sample required for that purpose is usually the peripheral blood of the order of several milliliters. The DNA is extracted from the leukocytes separated from the peripheral blood as the sample. Approximately five days are usually required from step 1 to step 6. In diagnosing the hereditary diseases, the pattern of a fraction from a person tested is compared with the pattern of a fraction from a normal person. The person tested is decided as normal when the pattern of the fraction from the person tested is determined to be identical to the pattern of the fraction from the normal person.

Recently, attempts have been made to conduct tests by using a probe DNA labelled with a fluorescent pigment, in place of a radioactive isotope, to excite the fluorescent pigment and to read the pattern of electrophoresis, from the point of view of safety and other environmental problems. However, highly sophisticated optical and signal processing techniques capable of detecting a faint magnitude of light are required to give a signal-to-noise ratio as equivalent as the radioactive isotope is employed, because the quantity of the sample required for diagnosis of the hereditary disease and determination of the sequence of bases is of the order of approximately $10^{-15}$ mole.

Japanese Patent Laid-open Publication (kokai) No. 62,843/1986 (corresponding to U.S. Pat. No. 4,675,059) discloses an electrophoresis apparatus of a fluorescence detecting type, capable of detecting a minute quantity of a sample labelled with a fluorescent pigment.

A description will now be made of such an electrophoresis apparatus based on fluorescence detection method.

FIG. 18 is a perspective view showing an outlook of a conventional electrophoresis apparatus of a fluorescent type. The electrophoresis apparatus comprises a combined electrophoresis and instrumentation unit 51 for implementing electrophoresis of a sample and measuring the distribution of fluorescence, a data processor 52 for performing data processing on the basis of measured data, and a cable 53 connecting the combined electrophoresis and instrumentation unit 51 to the data processor 52. The electrophoresis and instrumentation unit 51 has a door 51a through which a gel serving as a base for performing electrophoresis for DNA fragments and a predetermined quantity of a sample (DNA fragments) for electrophoresis are poured into the electrophoresis and instrumentation unit 51. As the door 51a is closed and a switch for starting electrophoresis on an operation display panel 51b is pressed to start electrophoresis. As the electrophoresis has been started, a monitor of the operation display panel 51b of the electrophoresis and instrumentation unit 51 displays an operational state. The data measured by the electrophoresis and instrumentation unit 51 is transmitted to the data processor 52 in which the data is processed on the basis of a predetermined program stored in advance. The data processor 52 comprises a computer body 54, a keyboard 55 for entering an instruction from the operator, a display unit 56 for displaying the processing state and results, and a printer 57 for recording the data-processed results.

FIG. 19 is a block diagram showing the configuration of the inside of the electrophoresis and instrumentation unit. As shown in FIG. 19, an overall configuration of the combined electrophoresis and instrumentation unit 51 (FIG. 18) comprises an electrophoresis unit section 63 and a signal processor unit section 64. The electrophoresis unit section 63 comprises an electrophoresis section 5 for implementing electrophoresis, a first electrode 2a and a second electrode 2b each for applying voltage to the electrophoresis section 5, a support plate 3 for supporting the electrophoresis section 5 as well as the first and second electrodes 2a and 2b, a power source unit 4 for applying voltage to the electrophoresis section 5, a light source 11 for emitting light for exciting a fluorescent substance, an optical fiber 12 for leading the light from the light source 11, a light collector 14 of an optic system for condensing and collecting fluorescence 13 generated by the fluorescent substance, an optical filter 15 for selectively passing the light having a particular wavelength therethrough, and an optical sensor 16 for converting the condensed light into electric signals. The signal processor unit section 64 comprises an amplifier 17 for amplifying the electric signals from the optical sensor 16, an analog-digital converting circuit 18 for converting analog signals of the electric signals into digital data, a signal processing section 19 for pre-processing the digital data, for example, by performing addition average processing or the like, an interface 20 for implementing interface processing for feeding the pre-processed data to an external data processor, and a control circuit 10 for implementing overall control of the electrophoresis unit section and the signal processing system. The digital signal OUT generated from the signal processor unit section 64 is transmitted to the data processing unit 52 (FIG. 18), thereby implementing the data processing such as analysis processing and so on.

A description will now be made of the operation of the electrophoresis apparatus with reference to FIGS. 18 and 19.

After the door 51a of the electrophoresis and instrumentation unit 51 is opened, a gel is poured into the electrophoresis section 5 disposed within the combined electrophoresis and instrumentation unit 51 and thereafter a sample of DNA fragments labelled with a fluorescent substance is poured thereinto. As a switch of the instrument panel 51b is pressed to give an instruction to start electrophoresis, then voltage is applied from the first and second electrodes 2a and 2b of the power source unit 4 to the electrophoresis section 5, thereby starting the electrophoresis. The electrophoresis allows the sample labelled with the fluorescent substance to migrate, for example, in lanes 71, 72, 73 and 74, as shown in the schematic representation 70 of FIG. 22, gathering the molecules having the same molecular weights together forming bands 66. The molecules having lower molecular weights migrate faster than those having higher molecular weights so that the former migrates in a distance longer than the latter within the same time unit. The bands 66 are detected in a manner as shown in FIG. 20a by leading light from the light source through the optical fiber 12 to a light path 61 and irradiating the gel on the light path 61 with the light, exciting the labelled fluorescent substance concentrated on the bands 66 in the gel to generate fluorescence 13, and detecting the fluorescence 13. The fluorescence 13 generated contains the fluorescent substance in the concentration as extremely low as approximately $10^{-16}$ mole per band, although the quantity of fluorescence may depend upon an extinction coefficient of the fluorescent substance used, quantum efficiency thereof, intensity of exciting light, etc. For instance, fluorescein isothiocyanate has a peak of the wavelength of excitation at 490 nm, a peak of its fluorescent wavelength of 520 nm, an extinction coefficient of $7 \times 10^4$ mole$^{-1}$·mole$^{-1}$, and a quantum efficiency of approximately 0.65. If fluorescein isothiocyanate employed exists in the concentration of $10^{-16}$ mole per band, the fluorescence generated contains photons of the order as low as $10^{10}/S$, when calculated by postulating the use of argon ion laser of a wavelength of 488 nm at output of 1 mW as a fluorescent substance, although it may vary to some extent with the thickness of the gel or the like. Hence, an extremely faint magnitude of fluorescence is required to be detected.

Referring to a front view as shown in FIG. 20a and to a longitudinally sectional view as shown in FIG. 20b, the electrophoresis section 5 comprises a gel member 5a composed of polyacrylamide or the like and gel supporting members 5b and 5c, each made of glass for supporting and interposing the gel member 5a from the both sides. A sample of DNA fragments is poured into the gel member 5a of the electrophoresis section 5 from its upper portion and the electrophoresis is carried out by applying voltage for electrophoresis to the first electrode 2a and the second electrode 2b (FIG. 18). While the electrophoresis is being carried out, the fluorescent substance contained in the bands of the pattern of electrophoresis in the gel member 5a along the light path 61 is irradiated with rays of light sent out from the light source, such as laser light, which pass through the optical fiber 12 onto the light path 61 of the gel member 5e. This allows the fluorescent substance present on the light path 61 to be excited to emit fluorescence 13 that is led to a light collector 14 of optics consisting of a combination of lenses and then selected by the optical filter 15 after having been condensed, followed by conversion into electric signals by means of a one-dimensional optical sensor 16. In order to convert a faint quantity of light into electric signals in an efficient fashion, the light is amplified to $10^4$ to $10^5$ times with an image intensifier or the like, and the image is converted into electric signals by the optical sensor 16, such as a one-dimensional optical sensor of CCD or the like. The electric signals converted by the optical sensor 16 are then amplified to signals of a desired level by the amplifier 17, and the analog signals are converted into digital signals by the analog-digital converting circuit 18, followed by transmission to the signal processing section 19. The digital signals transmitted from the analog-digital converting circuit 18 are then subjected to signal processing, such as addition average processing, or the like, in order to improve the signal-to-noise ratio (an S/N ratio), and the resulting digital data is transmitted to the data processor unit section 52 through the interface 20.

FIGS. 21a and 21b are schematic representations for describing an example of signals of a pattern indicative of the fluorescent intensity of DNA fragments transmitted from the electrophoresis and instrumentation unit 51. For instance, as shown in FIG. 21a, the fluorescent substance present on the light path 61 is excited upon irradiation of the gel member 5a of the electrophoresis section 5 with the laser light in the course of electrophoresis, thereby emitting fluorescence. The fluorescence is detected at predetermined positions of each lane in the direction of electrophoresis, as indicated by 62, as the time of electrophoresis elapses. In other words, the fluorescence is detected as the bands 66 of each lane pass through the positions of the light path 61, thereby detecting a pattern signal of fluorescence intensity in each of the lanes, as shown in FIG. 21b. As a peak of the fluorescence intensity is given When each of the bands 66 passes through the positions of the light path 61, the pattern signal of the fluorescence intensity as shown in FIG. 21b represents a pattern signal indicating the magnitude of fluorescence intensity of the bands 66 located in the direction of electrophoresis, as indicated by 62. In other words, the pattern signal constitutes a profile wave form proportional to the concentration of fluorescence, and a sequence of the bases of a DNA fragment may be determined by deciding a peak value of the pattern signal.

The computer body 54 of the data processing unit 52 implements data processing for comparing molecular weights and determining a sequence of bases of a DNA fragment on the basis of data of the pattern indicative of fluorescence intensity in response to data of the pattern signals for the fluorescence intensity of the DNA fragments transmitted from the electrophoresis and instrumentation unit 51. The sequence of the bases and so on determined by the data processing is symbolized and then generated, thereby displaying the symbolized data on a display screen by the display unit 56 or printing it out by the printer 57.

The aforesaid embodiment is directed to an example of the apparatus in which the fluorescent pigment is employed for labelling the sample. Japanese Patent Laid-open Publication (kokai) No. 167,649/1989 discloses another example of an apparatus capable of reading a fluorescent pattern of electrophoresis. This apparatus is of such a type as reading a fluorescent pattern of the electrophoresis section as a whole after the end of electrophoresis, unlike the aforesaid electrophoresis apparatus of such a type as reading the distribution of the fluorescent pattern passing through a reading section in the course of electrophoresis.

It is to be noted herein that the gel electrophoresis method employed for the electrophoresis pattern reading apparatuses on the basis of the fluorescence detection method is the same as the gel electrophoresis method which has been employed for the conventional apparatuses in which the sample is labeled with the radioactive isotope. The gel electrophoresis method may cause a warp in the pattern of electrophoresis because a speed of migration of bands may vary with the position of an electrophoresing plate due to irregularities in temperatures within the gel and for other reasons, thereby causing a warp in the pattern of electrophoresis. Hence, for example, when electrophoresis of two kinds of samples or electrophoresis in a two-dimensional way is to be performed with the purpose to compare two kinds of patterns of electrophoresis for the diagnosis of hereditary diseases, the positions of the electrophoresed bands may be deviated between the results of electrophoresis due to the warp and a comparison between the two patterns of electrophoresis may be rendered difficult, even if either of the methods for labelling the samples with the radioactive isotope or with the fluorescent substance would be adopted, as long as the conventional gel electrophoresis method is employed. Further, implementation of the correction of such patterns of electrophoresis by means of data processing is also rendered laborious and complex.

Further, as the electrophoresis and instrumentation unit for implementing electrophoresis and simultaneously measuring the distribution of the fluorescent substance passing through the reading unit adopts two-dimensional electrophoresis, it requires the one-dimensional electrophoresis to be implemented by one device and the two-dimensional electrophoresis to be conducted by another device, so that this operation is laborious and complex.

SUMMARY OF THE INVENTION

The object of the present invention is to provide a multi-colored electrophoresis pattern reading system suitable for a comparison between a plurality of patterns of electrophoresis by labelling each of plural samples with a fluorescent pigment having a different fluorescence wavelength, subjecting the plural samples to electrophoresis simultaneously, and reading the resulting patterns of electrophoresis.

Another object of the present invention is to provide a multi-colored electrophoresis pattern reading system capable of reading the fluorescent patterns of the patterns of electrophoresis and comparing the patterns of electrophoresis without undergoing a warp resulting from electrophoresis.

In order to achieve the aforesaid objects, the present invention consists of a multi-colored electrophoresis pattern reading system capable of labelling each of plural samples separately with each of plural fluorescent substances having a different fluorescent wavelength, subjecting the plural samples to electrophoresis to develop a pattern of electrophoresis, exciting the fluorescent substances labelled on the respective plural samples to emit fluorescence, and reading a fluorescent pattern emitting the fluorescence, characterized by: a light source means for irradiating the pattern of electrophoresis with irradiating light for exciting the fluorescent substance labelled on the sample; a light scanning means for scanning the irradiating light from the light source means and irradiating a gel in the direction of thickness of the gel with the irradiating light; a light receiving means for receiving the fluorescence resulting from the pattern of electrophoresis by separating from scattered light resulting from a reading surface on the basis of a position relationship of a light receiving path by setting a light receiving surface in a direction different from an optical axis of irradiating light; a fluorescent-wavelength separating means for separating fluorescent having a predetermined wavelength from optical signals received by the light receiving means by the aid of an optical filter capable of controlling an angle of incidence relative to the optical axis of the optical filter; an optoelectric conversion means for generating electric signals by subjecting the optic signals passed through the fluorescent-wavelength separating means to optoelectric conversion; and a signal processing means for processing the electric signals from the optoelectric conversion means to thereby convert them into a predetermined form of data representation.

The light source means is a light source for generating irradiating light for emitting fluorescence by exciting two or more fluorescent substances and more labelled separately on the samples. In order to give light of wavelength for exciting each of the fluorescent substances, for example, a plurality of light sources may be provided to generate a mixture of light from the plurality of the light sources. The light source means may be a single light source when the light resulting from the single light source has a predetermined range of wavelengths. The light scanning means is arranged to scan the irradiating light from the light source means and radiate in the direction of thickness of the gel. The light receiving means has its light receiving surface set in the direction different of the optical axis of the irradiating light and is designed so as to receive the fluorescence from the pattern of electrophoresis separated from the scattered light from the reading surface due to the position relationship of a light receiving path. The fluorescent-wavelength separating means has the optical filter capable of controlling the angle of incidence of fluorescence relative to the optical axis of the optical filter and it is to separate the predetermined fluorescent wavelength from the optical signals received by the light receiving means by taking advantage of dependence of the optical filter upon a pass band angle by controlling the angle of incidence of fluorescence to the optical filter. The optoelectric conversion means generates the electric signals by optoelectrically converting each of the optical signals separated by the fluorescent-wavelength separating means and the signal processing section processes the electric signals from the optoelectric conversion means, thereby converting them into the predetermined form of data representation.

The signal processing section has an integral circuit composed of a condenser and a switch for controlling an integral operation and it can control the integral operation of the integral circuit in synchronization with the scanning of the irradiated light by the optically scanning mechanism, and the integral time and the number of scans for reading may be altered in accordance with the angle of incidence of the optical signals controlled by the optical filter of the fluorescent-wavelength separating section. This operation allows the integral operation for the faint electric signals so as to correspond to the scanning of the irradiated light. At this time, the speed of the integral operation corresponds to the speed of scanning the irradiated light, so that the pattern of electrophoresis can be read by amplifying faint outputs of fluorescence in an efficient way.

The multi-colored electrophoresis pattern reading system having the configuration as described above can read the distribution of the fluorescent substances by the difference in wavelength of fluorescence inherent in the fluorescent pigments from the patterns of electrophoresis of the samples. Further, the multi-colored electrophoresis pattern reading system according to the present invention allows all the samples, including the comparative sample, to undergo an equal degree of a warp due to electrophoresis, so that the results of electrophoresis can be read without paying attention to the warp originating from electrophoresis.

Other objects, features and advantages of the present invention will become apparent in the course of the description of the preferred embodiments, which follows, with reference to the accompanying drawings.

DESCRIPTION OF THE PREFERRED EMBODIMENTS

Figure 1:
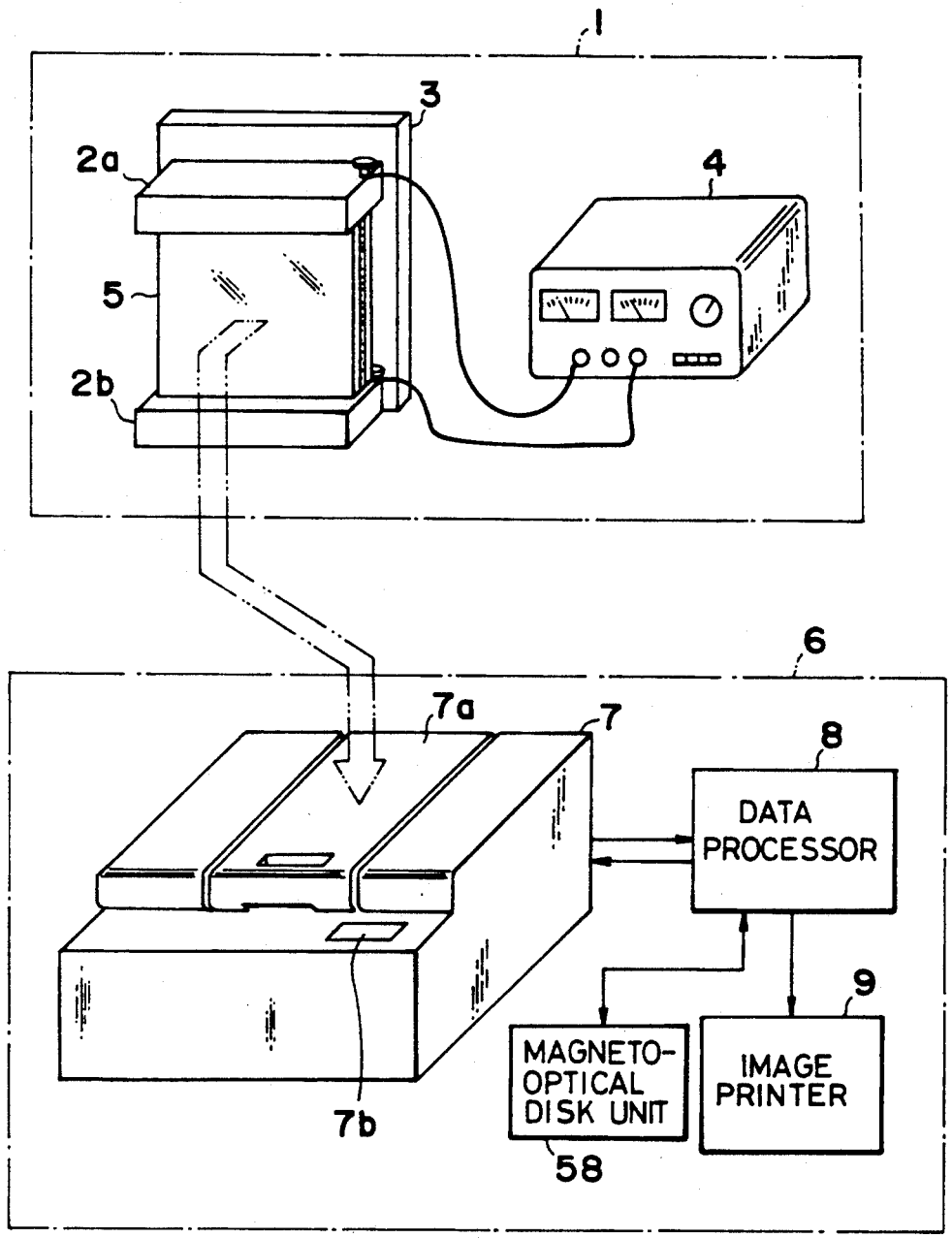
FIG. 1 is a schematic representation showing an overall configuration of the electrophoresis pattern reading system of a fluorescent type according to an embodiment of the present invention.

FIG. 1 is a schematic representation showing the overall configuration of the electrophoresis pattern reading system of a fluorescent type according to an embodiment of the present invention.

Figure 20A:
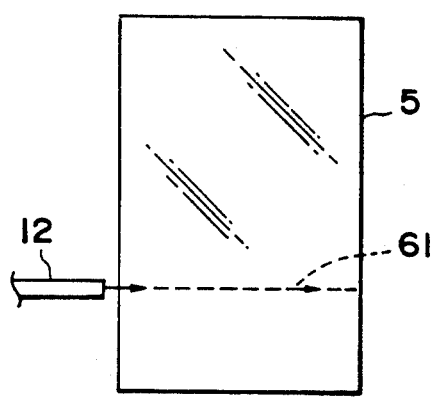
FIGS. 20a and 20b are elevational view and a longitudinally sectional view showing the electrophoresis unit, respectively, in order to describe the principle of the operations for detecting the pattern of electrophoresis by the fluorescence method.
Figure 20B:
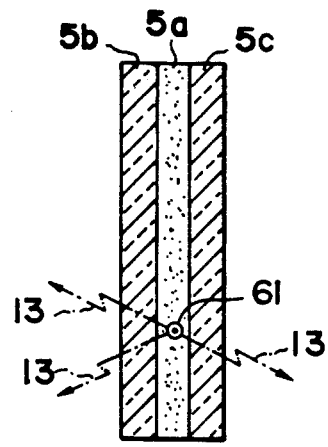

As shown in FIG. 1, the multi-colored electrophoresis pattern reading system of a fluorescent type according to the present invention comprises a combination in which an electrophoresis unit 1 is interconnected to a reading unit 6 disposed separately from the electrophoresis unit 1. The electrophoresis unit 1 comprises an electrophoresis unit section 5, a first electrode 2a, a second electrode 2b, a supporting plate member 3, and a power source 4 for electrophoresis. The electrophoresis unit section 5 consists of a gel member serving as a base for electrophoresis and a gel support member for supporting the gel member by a glass panel or the like for interposing the gel member and it is mounted to the first and second electrodes 2a and 2b which in turn apply voltage for electrophoresis to the electrophoresis unit section 5. The supporting plate member 3 is arranged to support the electrophoresis unit section 5 as well as the first and second electrodes 2a and 2b. The power source 4 is to supply the voltage for electrophoresis. As described hereinabove, the electrophoresis unit section 5 is composed of the gel member for developing a sample for electrophoresis, such as polyacryl amide or the like, and the gel support member for supporting the gel member interposed from both sides by the glass plate panels or the like (see FIGS. 20a and 20b).

A sample of DNA fragments to be electrophoresed is fed from an upper portion of the gel member of the electrophoresis unit section 5 mounted to the electrophoresis unit 1, the voltage for electrophoresis is applied to the first and second electrodes 2a and 2b from the power source 4, thereby enabling electrophoresis of the sample to give a pattern of electrophoresis. The electrophoresis unit section 5 is removed or detached from the electrophoresis unit 1 after electrophoresis has been finished and mounted to the reading unit 6 for reading the resulting pattern of electrophoresis.

As the reading unit 6 is mounted to an instrumentation unit body 7 of the instrumentation unit in a state in which the electrophoresis unit 5 is subjected to electrophoresis or in a state in which only the gel member is removed from the electrophoresis unit section 5, the resulting pattern of electrophoresis is read and data is then processed by the reading unit 6. As shown in FIG. 1, the reading unit 6 has the instrumentation unit body 7 as an essential portion, and a data processor 8, an image printer 9 and other accessories such as a magneto-optical disk unit 58 mounted to the instrumentation unit body 7. The data processor 8 is arranged to implement data processing, image processing and determination processing for the data resulting from the electrophoresis pattern read by the instrumentation unit body 7. The image printer 9 is to process and print the read electrophoresis pattern data out. The instrumentation unit body 7 has a reading table disposed immediately below a lid 7a mounted at the upper portion of the instrumentation unit body for reading the pattern of electrophoresis from the electrophoresis unit section 5 consisting of the gel member and the gel support member, wherein the electrophoresis is performed.

After the electrophoresis unit section 5 is detached from the electrophoresis unit 1 after electrophoresis, the lid 7a disposed at the upper portion of the instrumentation unit body 7 is opened and the electrophoresis unit section 5 is then mounted to the reading table. After mounting the electrophoresis unit section 5 to the reading table, the lid 7a is closed and a start switch for starting the reading of the pattern of electrophoresis on an operational display panel 7b of the instrumentation unit body 7 is pressed, thereby starting reading the pattern of electrophoresis of the gel member of the electrophoresis unit section 5. As the reading of the electrophoresis pattern starts, the scanning of the irradiating light from a spot light source built in the instrumentation unit body 7 is started and the gel member of the electrophoresis unit section 5 is irradiated with the light for exciting a fluorescent substance, thereby emitting fluorescence. The fluorescence emitted upon irradiation with the light is received, and a pattern of distribution of the fluorescent substance is measured. The data processor 8 implements data processing of the data read and measured by the instrumentation unit body 7 and further controls the instrumentation unit body 7 itself. The processed data is printed out by the image printer 9. In this embodiment, the image printer 9 to be employed is of a type capable of printing with a plurality of colors, thereby permitting the electrophoresis pattern images to be printed out with multiple colors so as to correspond to the samples.

Figure 2:
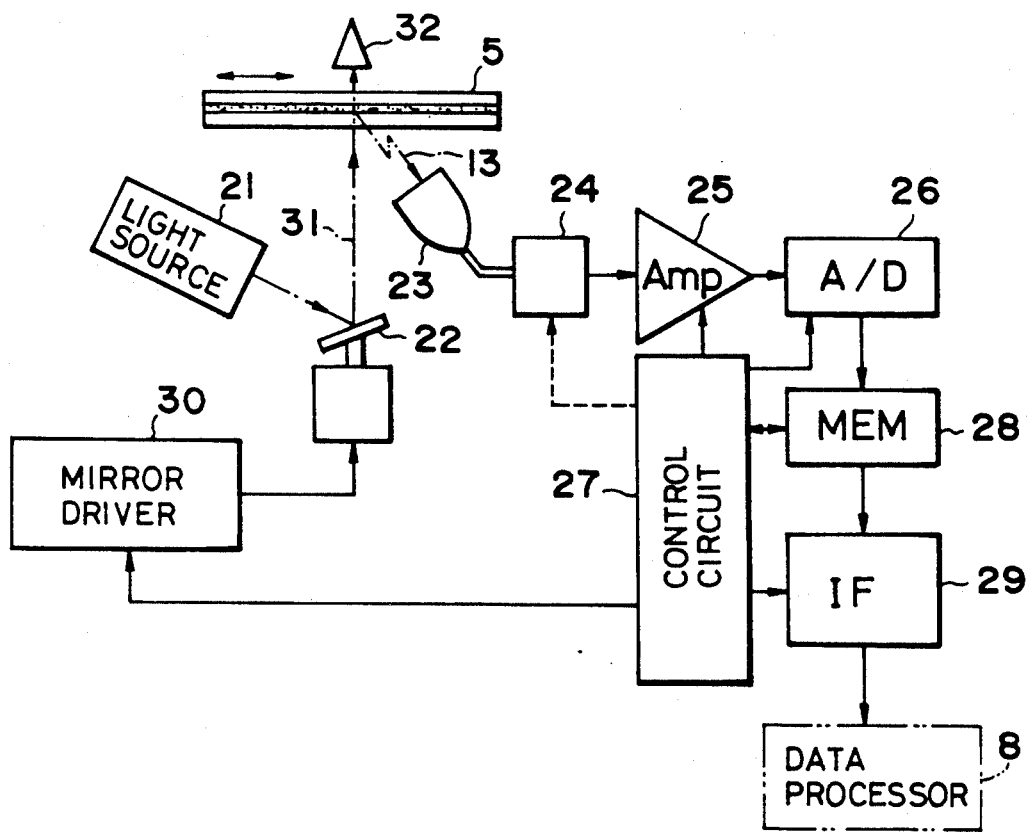
FIG. 2 is a block diagram showing the configuration of the essential portion of the instrumentation section body.
Figure 3:
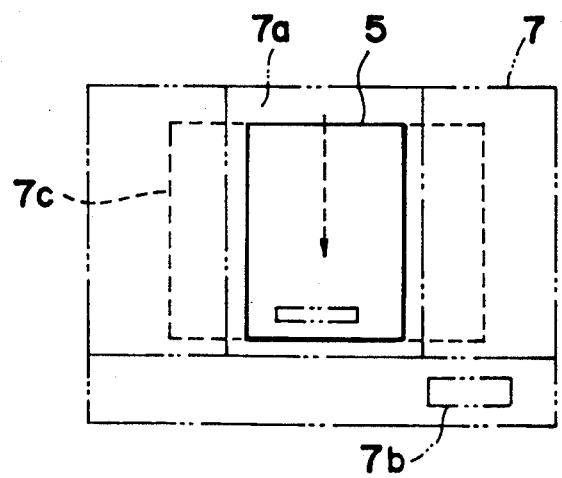
FIG. 3 is a view showing the position in which an electrophoresis unit to be mounted to the instrumentation section body.

FIG. 2 is a block diagram showing the configuration of the essential portion of the instrumentation unit body 7, and FIG. 3 is a view showing the position in which the electrophoresis unit to be mounted to the instrumentation section body 7.

In performing the analysis of each of plural samples by means of electrophoresis with the multi-colored electrophoresis pattern reading system of a fluorescent type, the samples of DNA fragments labelled with the fluorescent pigments or fluorescent substances are subjected to electrophoresis with the electrophoresis unit 1 for a predetermined period of time, for example, as long as approximately 5 hours. After the electrophoresis has been finished, the electrophoresis unit section 5 is detached from the electrophoresis unit 1 and the gel member of the electrophoresis unit section 5 removed therefrom is then mounted to an upper portion of the reading table 7c through the lid 7a of the instrumentation unit body 7 of the reading unit 6, as shown in FIG. 3, in such a state that the gel member is still interposed with the gel support member, such as glass plates, or in such a state that the gel support member is detached from the electrophoresis unit section 5. Then, the lid 7a is closed, thereby finishing the setting of the electrophoresis sample to the reading unit. When no gel member is yet labelled with the fluorescent pigment after electrophoresis, the gel member may be labelled therewith in this stage of mounting the pattern of electrophoresis. The gel may be dried before mounting to the reading table.

Then, operations are performed for instructing the start of reading the pattern of electrophoresis by pressing the read starting switch of the operation display panel 7b or by giving an instruction to start reading from the data processor 8. In starting the reading operations through the data processor 8, the state of mounting the electrophoresis unit section 5 to the instrumentation unit body 7 is transmitted through a control signal line to the data processor 8 which in turn controls the operations of the reading unit section of the instrumentation unit body 7 after the state in which the electrophoresis unit section 5 is mounted has been confirmed. In this case, parameters such as reading speed and so on during operations may be set and registered in advance on the side of the data processor 8, thereby allowing the operations for starting the reading to be performed automatically and reducing burdens for operating the switches on the side of an operator. The read data on the distribution of the fluorescent pigments is transmitted to the data processor 8 which in turn implements desired processing programmed in advance, such as processing for detecting a peak of the intensity of fluorescence, electrophoresis distance, and so on. The data of the processed results is printed out, when needed, by the image printer 9 as image having a shade of color in accordance with the intensity of fluorescence or as image in which the intensity of fluorescence is divided by contour lines, colors or concentrations of color. The image having the shade of color in accordance with the intensity of fluorescence looks equal to an X-ray film image of data obtained by labelling the sample with a radioactive isotope in conventional manner and subjecting the sample to electrophoresis. The data of the results after data processing may be stored, when needed, as digital data in a magnetically or optically recording device.

Figure 7:
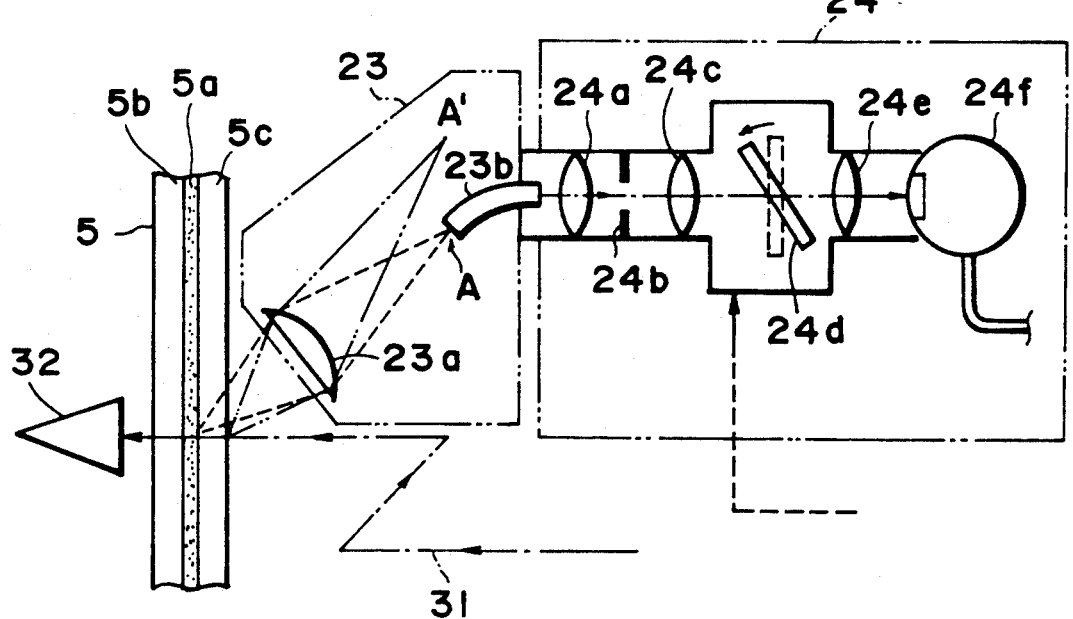
FIG. 7 is a schematic representation showing the detail configuration of the optic system in a light collector and an optoelectric conversion section.

Referring to FIG. 2 showing the configuration of the instrumentation unit body 7, laser beams, as indicated by 31, emitted from the light source 21 are scanned in the direction from the front to the rear in the drawing with the vibrating mirror 22 to be driven by the mirror driver 30 and the gel member as an object of reading is exposed to the laser beams 31. The spot lights of the laser beams 31 scanned by the vibrating mirror irradiates the gel member of the electrophoresis unit section 5 in the direction of thickness of the gel member thereof while moving. The gel member of the electrophoresis unit section 5 emits fluorescence upon irradiation with the spot lights of the scanned laser beams 31. The resulting fluorescence, as indicated by 13, with the spot lights of the laser beams, as indicated by 31 are received by the light collector 23. The light collector 23 is arranged to have a light path for receiving fluorescence 13 and an optical axis to be deviated from the optic axis of the spot light thrown on the electrophoresis unit section 5, and the optical lens system is arranged in a position relationship to the light path for receiving the fluorescence 13 so as to receive fluorescence, as indicated by 13, with enhanced sensitivity to separate fluorescence from the scattered light emitted from the irradiated surface of the electrophoresis unit section 5. The light received by the light collector 23 is converted into electric signals by the optoelectric conversion section 24 and then amplified by the amplifier 25. The optoelectric conversion section 24 has the fluorescent-wavelength separating section for selectively separating the light having the predetermined wavelength and it can function as converting the fluorescence having the predetermined wavelength into electric signals. As will be described hereinafter, the fluorescent-wavelength separating section is provided with a mechanism for rotating the optical filter for controlling the angle of incidence of the optical filter relative to the optical axis thereof by operatively rotate the optical filter by the aid of the control circuit 27. In the fluorescent-wavelength separating section, as shown in FIG. 7 the angle of incidence of the optical filter is controlled by the mechanism for rotating the optical filter, thereby separating the fluorescence having the predetermined wavelength from the optical signals received by the optically receiving section by taking advantage of dependence of the optical filter upon the pass band angle. An optic trap 32 is mounted on the side opposite to the surface of the electrophoresis unit section 5 to be irradiated with the laser beams 31 in order for the laser beams 31, as stray light, to cause no adverse influence upon the surface of the electrophoresis unit section 5 after transmission through the gel member.

The light collector 23 receives the fluorescence 13 and passes it through the optoelectric conversion section 24 with enhanced sensitivity to receiving of the fluorescence 13 to be detected, and the fluorescence 13 received is then converted through the optoelectric conversion section 24 into electric signals which in turn are amplified by the amplifier 25 and entered into the analog-digital conversion circuit 26, whereby the electric signals are converted into digital data. The signals detected from the fluorescence and converted into digital data is stored by the memory 28 and transmitted to the data processor 8 through the interface control circuit 29. The overall control over a series of the signal processing as described hereinabove is carried out by the control circuit 27.

A description will now be made of the configuration of each portion of the instrumentation unit body of the electrophoresis pattern reading system (as shown in FIG. 2).

Figure 4:
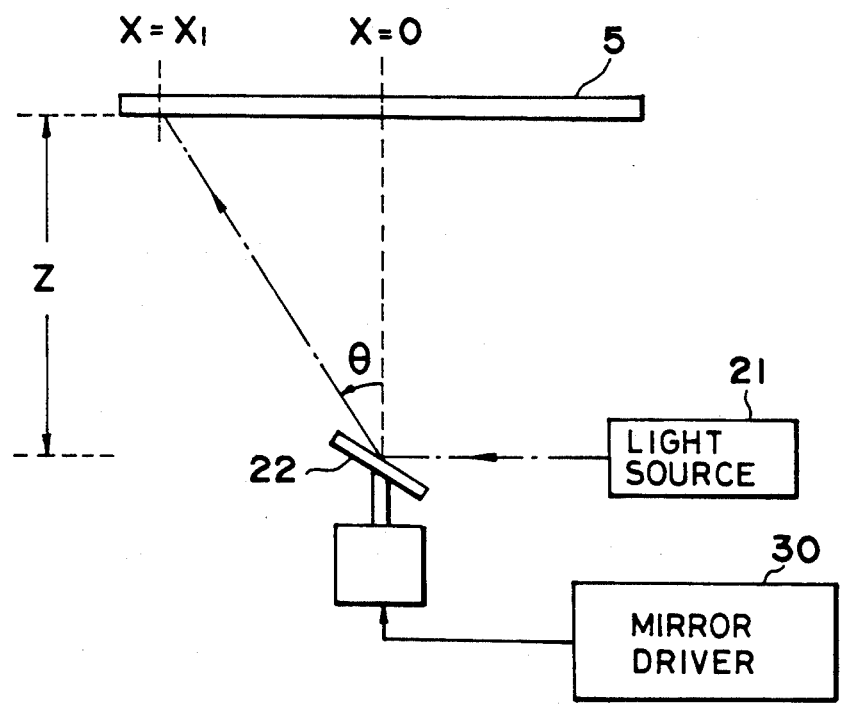
FIG. 4 is a view showing the light scanning mechanism for scanning a gel surface with laser beams by using a vibrating mirror.
Figure 5:
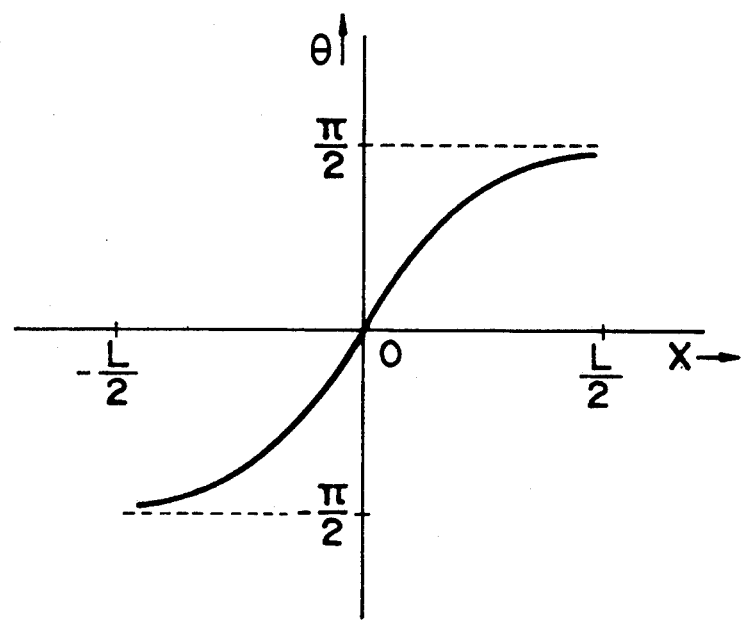
FIG. 5 is a graph showing the relationship between the angles of rotation of the vibrating mirror and the distance in which spot light of the laser beams moves.

FIG. 4 is a view showing the light scanning mechanism for scanning a gel surface with laser beams by using the vibrating mirror and FIG. 5 is a graph showing the relationship between the angles of rotation of the vibrating mirror and the distance in which spot light of the laser beams moves.

As shown in FIG. 4, the light source 21 and the vibrating mirror 22 are disposed in the positions relative to the electrophoresis unit section 5. This position relationship causes the light spot to move at the both end portions of the electrophoresis unit section 5 at a speed faster than at the portion in the vicinity of the central portion thereof (X=0), for example, when the vibrating mirror 22 is driven by the mirror driver 30 so as to vibrate at an isometric speed. This causes the difference in sensitivity to detect fluorescence to be detected between the central portion of the sample of the electrophoresis unit section 5 and its end portion. Hence, in this embodiment, the speed of driving the vibrating mirror 22 is corrected in order to move the spot light of the laser beams at an equal speed on the gel member of the electrophoresis unit section 5. In other words, the relationship between the position X of the spot light and the angle $\theta$ of the vibrating mirror 22 is set as shown in FIG. 5. The angle $\theta$ of the vibrating mirror 22 is represented by the following:

$$\theta = \arctan(X/Z)$$

where
X is the distance in the plane direction having the point as origin, a point from which the phantom line extends vertical to the surface of the gel member of the electrophoresis unit section from the center of rotation of the vibrating mirror 22; and Z is the distance from the center of rotation of the vibrating mirror 22 to the gel member of the electrophoresis unit section 5.

The angle of rotation and the distance of movement for the light scanning mechanism of this type may be corrected by a fθ lens, however, the fθ lens is expensive and the unit for mounting the fθ lens becomes heavy as a whole. In this embodiment, the mirror driver 30 is provided with a control circuit for implementing control of variables of the speed of rotating the vibrating mirror 22 to control the speed of driving the rotation of the vibrating mirror 22 of the light scanning mechanism and the distance of moving the vibrating mirror 22 thereof, thereby correcting the angle of rotating the vibrating mirror 22 thereof.

Figure 6:
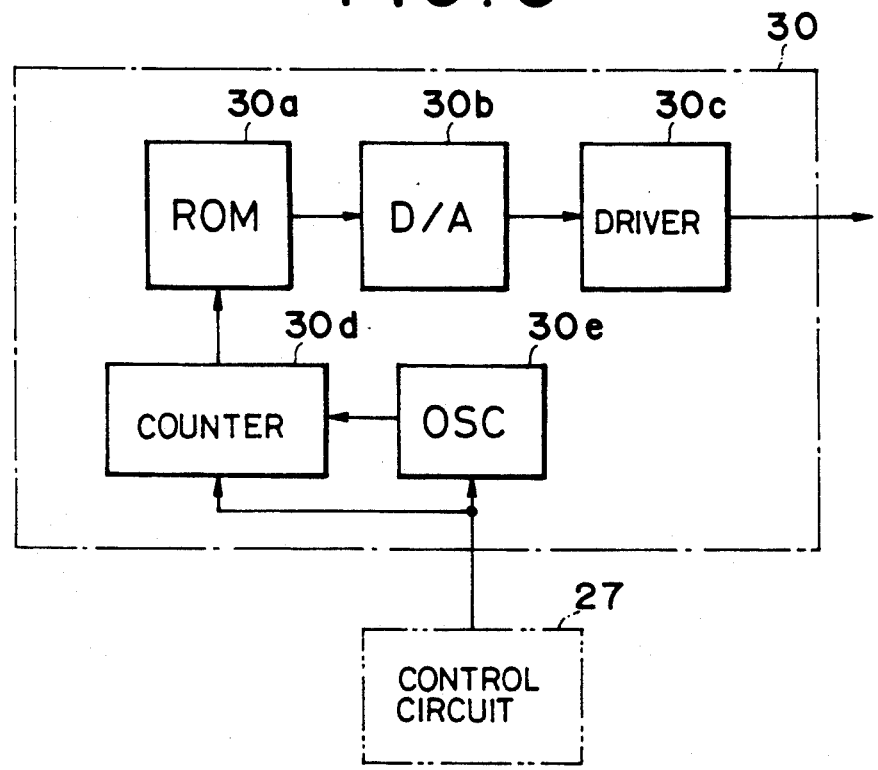
FIG. 6 is a block diagram showing the configuration of the essential portion of the control circuit for controlling a mirror driver for controlling the rotation of the vibrating mirror.

FIG. 6 is a block diagram showing the configuration of the essential portion of the circuit for controlling a mirror driver for controlling the rotation of the vibrating mirror 22. A linear motor is employed as an actuator for the vibrating mirror 22, and the angle of rotating the vibrating mirror 22 can be controlled by applying voltage in proportion to the angle of rotation. In order to allow the spot lights of the laser beams to move at equal speeds on the surfaces of the gel member, the distance X of the surface thereof is so set as to become proportional to the time t. As the relationship between the angle θ of rotating the vibrating mirror and the distance X of moving the spot lights is as shown in FIG. 5, there is generated a signal in a wave form indicative of voltage corresponding to the graph of FIG. 5 wherein the axis of abscissas indicates the time and the axis of ordinates indicates the voltage and this signal serves as controlling the driving of the vibrating mirror 22. The generation of the control signal is controlled by the control circuit of the mirror driver 30, and the control signal is fed to the actuator of the vibrating mirror 22 for controlling the driving of the vibrating mirror 22.

As shown in FIG. 6, the mirror driver 30 comprises a read-only memory 30a having functional wave forms stored therein, a digital-analog conversion circuit 30b for converting the read function data into voltage signals, a driver 30c for amplifying the converted voltage signals and generating a control signal for controlling the drive of the mirror driver 30, a counter 30d for giving read addresses in time series to the memory 30a, and an oscillating circuit 30e for providing the counter with clock signals.

The oscillating circuit 30e is operated by an instruction from the control circuit 27 of the instrumentation unit body 7, and clock signals are entered into the counter 30d from the oscillating circuit 30e, thereby counting the clock signals and generating the read addresses to be fed to the read-only memory 30a in time series. As the read addresses generated by the counter 30d are fed to the read-only memory 30a in time series, the function data stored in advance is read out one after another from the read-only memory 30a. In the read-only memory 30a is in advance written the function data (as shown in FIG. 5) relating to the angles of rotation of the vibrating mirror 22, and such function data is read in time series. In this example, the number of bits of the function data is 12 bits, and the function data to be read out is converted by the digital-analog conversion circuit 30b into voltage signals of analog signals for controlling the angle of rotation of the vibrating mirror 22. The voltage signals are processed to remove noises in a step type by filtering with the mirror driver 30. After the voltage signals are then amplified, they are fed to the vibrating mirror 22, thereby allowing the vibrating mirror 22 to be rotated at a desired angular speed so as to become constant in the speed of moving (scanning) the spot lights of the laser beams on the electrophoresis unit section.

The scanning speed is so set as to be variable at 0.5 Hz, 1 Hz, 2 Hz, 5 Hz, 10 Hz, 20 Hz, 50 Hz, 100 Hz and 200 Hz in order to become approximately logarithmically equal. This arrangement permits an efficient reading by changing the reading speeds in accordance with the quantity of the fluorescent substances for use in labelling the samples for electrophoresis or the difference in the quantum efficiency of the fluorescent substances. The scanning speed can be specified through the operation display panel 7b or the data processor 8 by transmitting specification data from the control circuit 27 to the mirror driver 30 and controlling the counter 30d and the oscillating circuit 30e, thereby driving the vibrating mirror 22 at a desired scanning speed.

By implementing the control of driving the vibrating mirror 22 in the way as described hereinabove, the laser beams from the light source 21 are scanned and radiated as spot lights capable of moving on the electrophoresis unit section 5 at a constant speed. The irradiation of the gel member of the electrophoresis unit section 5 with the laser light excites the fluorescent substance present in the gel member irradiated with the laser light, thereby emitting fluorescence as indicated by 13.

FIG. 7 shows the configuration of the essential portions of the light collector 23 for receiving the light generated from the gel member and of the optoelectric conversion section by focusing their light pathways. As described hereinabove, the gel member of the electrophoresis unit section 5 is interposed between the gel support members 5b and 5c, and each of the gel support members 5b and 5c is composed of boron silicate glass plates having a relatively less magnitude of fluorescence in this embodiment, although quartz glass plates or various optical glasses can also be employed as the gel support members 5b and 5c. As shown in FIG. 7, as the electrophoresis unit section 5 is irradiated with laser beams 31 which moves while being scanned, the light of the laser beams 31 is thrown on the gel support member 5c and transmits through the gel support member 5c in the direction of its thickness, reaching the gel member 5a through which in turn the irradiated light of the laser beams 31 advances in the direction of its thickness and the light transmits through the gel member 5a and then the gel member 5b. Each of the gel support members 5b and 5c is approximately 5 mm thick, and the gel member 5a is approximately 0.35 mm thick. The light of the laser beams 31 thrown on the gel support members 5b and 5c as well as the gel member 5a is so set as to reach the gel member 5a at a substantially equal light intensity in any position of the electrophoresis unit section 5. Further, the expansion of laser beams 31 or the reduction in its intensity due to scattered light to be caused on the plane of incidence of the irradiating light for the gel member 5a as well as the gel support members 5b and 5c can be decreased to a remarkable extent because their radiating light is thrown on in the direction perpendicular to the plane in the direction of thickness. Furthermore, the laser beams 31 are damped down by the optical trap 32 after transmission through the gel member, in order to cause no adverse influence as stray light.

The fluorescence is generated from the inside of the gel member 5a by scanning the exciting light in the manner as described hereinabove, and the fluorescence is collected by the light collector 23, together with scattered light by the exciting light. The scattered light generated in the gel support members 5b and 5c is separated in a geometrical-optical way by the position relationship of the light path for receiving the light, thereby extracting only the fluorescence from the gel member and transmitting it to the optoelectrical conversion section 24. The fluorescence are separated from the scattered light by a separator 24d of the fluorescent-wavelength separating section, and only the fluorescence separated from the gel member is transmitted to an optoelectrically converting element 24f. The separator 24d may be the optical filter or a diffraction grating having the same function. As the optoelectrically converting element 24f, there may be employed a photomultiplier or the like, which can amplify a faint magnitude of fluorescence and convert it into electric signals.

A description will now be made of the configuration of the optic system in the light collector 23 and in the optoelectrical conversion section 24 with reference to FIGS. 7 and 8.

As shown in FIG. 7, the light collector 23 is so arranged as to have such an optical pathway as collecting the fluorescence resulting from the electrophoresis unit section 5 and scattered light of the irradiating light resulting from the gel support members 5b and 5c by means of a cylindrical lens 23a. The scattered light and fluorescence from the electrophoresis unit section 5, which were received by the cylindrical lens 23a, are formed as image on the side opposite to the cylindrical lens 23a. In FIG. 7, the point A is a focal point of the fluorescence resulting from the gel member 5a and of the scattered light of the exciting light generated from the gel member 5a. On the other hand, for example, the scattered light of the exciting light generated on the surface of the gel support member 5c can form image at the focal point A'. It is to be noted herein that the fluorescence can be separated from the scattered light resulting from the gel support members in a geometrical-optical manner due to the position relationship of the light path for receiving the light by disposing the optical fiber array 23b at the focal point A so as to receive the fluorescence from the gel member 5a. In the method for irradiating the gel member with the irradiating light in the direction of thickness of the gel member, a quantity of scattered light emitted in the boundary surfaces becomes very small because the refractive index of the gel member is approximately as low as 1.4 to 1.5 and relatively close to the refractive index of the gel support members, such as glass plates, and the gel member is closely attached to the gel support members to thereby form a tight boundary surface between them. Hence, the light received at the point A contains a lesser quantity of the scattered light of the exciting light emitting from the surface of the gel member 5a, while it contains a larger rate of fluorescence emitting from the inside of the gel member 5a.

When the irradiating light is scanned directly on the gel member 5a from which either one of or both of the gel support members 5b and 5c is or are removed, the scattered light may emit from the surface of the gel member in the quantity nearly equal to the quantity emitting from the surface of the glass plate panel as the gel support member. In this case, the glass plate of the reading table (7c in FIG. 3) of the instrumentation unit body 7 demonstrates substantially the same effect as the glass plate panel of the gel support member, thereby suppressing the detecting sensitivity from reducing to a great extent and permitting the fluorescence emitting from the surface of the gel member to be detected with high efficiency. It is to be noted herein that, if either of the gel support member 5b or 5c or both of the gel support members 5b and 5c is or are removed, the gel member 5a is colored at this time. Particularly, when the gel support members 5b and 5c are not required to be removed, it is preferred to read the gel member 5a in such a state that the gel member 5a is interposed between the gel support members 5b and 5c, because this operation can improve a signal-to-noise ratio.

Although only one cylindrical lens is employed for the light collector 23 in this embodiment, another cylindrical lens may be disposed at the position symmetrical to the surface on which the laser beams are scanning or on the side opposite to the sample side. Further, for example, if a quantity of detectable fluorescence lacks, cylindrical lenses and optic fiber arrays may be disposed at four positions so as to encircle the scanning line of the gel member emitting fluorescence, thereby increasing the quantity of light to be collected and enhancing the magnitude of fluorescence to be detected. In this case, it is effective to deviate the optic axes so as to cause no reflection from the surface of the cylindrical lens to adversely affect the cylindrical lens facing the other one.

The fluorescence collected by the optical fiber array 23b is led to each of the optic fibers of the optical fiber arrays 23b, and the optic fibers are combined and entered into optoelectric conversion section 24. The fluorescence entered into the optoelectric conversion section 24 from the optical fiber array 23b is so processed as to extract its parallel light components only by a first lens 24a, a diaphragm 24b and a second lens 24c and the optical pathway is so arranged as for the parallel light components to enter into the fluorescent-wavelength separating section of the optical filter 24d. The optical filter 24d of the fluorescent-wavelength separating section is disposed to be associated with a mechanism for driving the rotation of the optical filter (as shown in FIG. 8) so as to allow control of the angle of incidence of the filter surface at an angle not normal to the direction in which the light travels. Only the fluorescent ingredient having the predetermined wavelength is selected in the fluorescent-wavelength separating section by the optical filter 24d whose angle of incidence is controlled at the predetermined angle, and the selected fluorescent ingredient is collected by a third lens 24e, thereby leading to the photomultiplier of the optoelectrical conversion element 24f and converting the detected fluorescence into electric signals.

Figure 8:
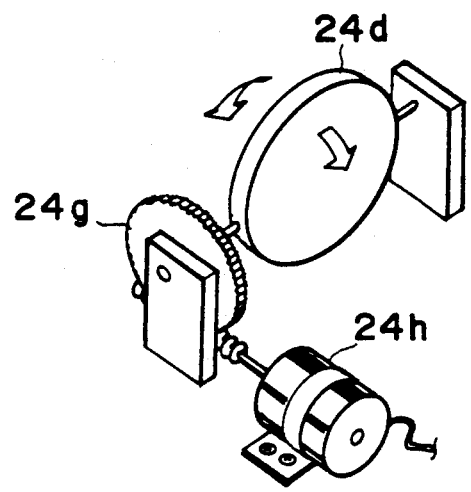
FIG. 8 is a schematic representation showing an example of a mechanism for driving the rotation of an optical filter capable of changing an angle of incidence of fluorescence relative to the optical axis of the optical filter.

As shown in FIG. 8, the fluorescent-wavelength separating section having such a mechanism as capable of driving the rotation of the optical filter 24d is provided with a mechanism for driving the rotation of the optical filter 24d so as for the surface of the optical filter 24d to change its angle relative to the optical axis of the optical filter 24d by controlling the control circuit 27. The mechanism for driving the optical filter 24d comprises a stepping motor 24h having a mechanism for detecting the position of the optical filter 24d and a gear mechanism 24g for transmitting the pivotal movement to the optical filter 24d. The pass band wavelength characteristic of the optical filter 24d is so arranged as to move toward the short wavelength side as the angle of incidence of light increases. Hence, the mechanism for rotating the optical filter 24d takes advantage of this characteristic to thereby change the angle of the surface of the optical filter 24d relative to the optical axis of the optical filter 24d and the fluorescence is received by changing the wavelength ingredient of the fluorescence obtainable through the optical filter 24d.

The optoelectrical conversion section 24 is provided with the fluorescent-wavelength separating section having the mechanism for driving the rotation of the optical filter 24d, thereby controlling the angle of incidence of the optical filter 24d to change the pass band wavelength characteristic, thereby appropriately selecting only the fluorescent wavelength to be received. Hence, the scattered light of the excited light can be removed to a sufficient extent, so that the configuration of the optoelectrical conversion section 24, such as lenses and restrictors, can be simplified.

Figure 9:
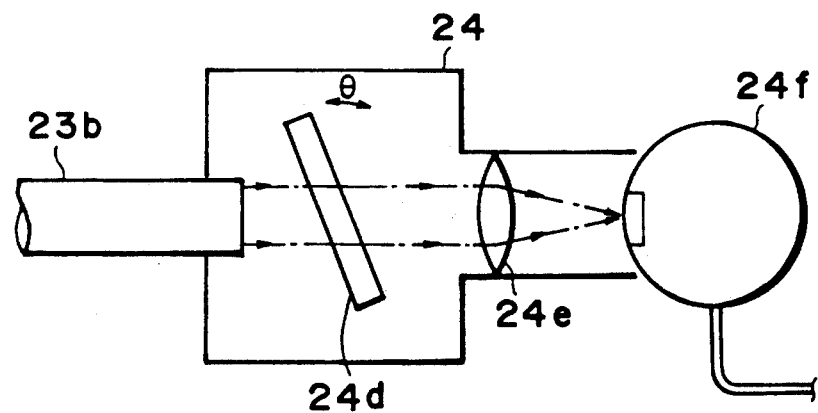
FIG. 9 is a schematic representation showing another example of the configuration of a simplified optoelectric conversion section.

FIG. 9 is a schematic representation showing an example of the simplified configuration of the optoelectrical conversion section 24. This optoelectrical conversion section 24 is provided with neither the first lens 24a nor the restrictor 24b nor the second lens 24c for extracting the parallel light. For the simplified configuration, the ingredient of the light reaching the incidence window of the photomultiplier of the optoelectrical conversion element 24f is arranged to be mostly parallel to the optical axis of the optical filter 24d. This configuration offers the advantage that the amount of the light to be detected can be increased to thereby enhance the sensitivity to detect the light because of the less number of parts of the optoelectrical conversion section which are to be disposed on the light path.

By separating the resulting fluorescence from the scattered light of the exciting light, the photomultiplier of the optoelectrical conversion element 24f can generate the electric signals corresponding to the intensity of fluorescence in accordance with the wavelength components of each fluorescence with the improved signal-to-noise ratio by controlling the angle of incidence of the fluorescence into the optical filter and selecting each of the fluorescent components having desired wavelengths. The resulting electric signals are entered into an amplifier 25 that amplifies faint signals to a sufficient extent in an amplification stage containing an integral circuit.

Figure 10:
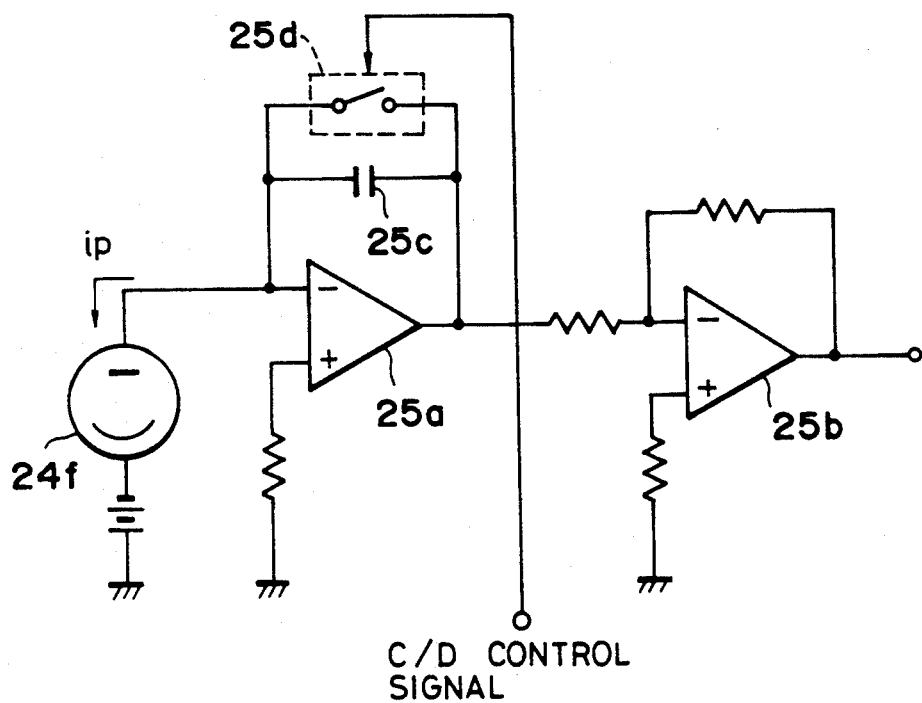
FIG. 10 is a circuit diagram showing the circuit configuration of an amplifier containing an integral circuit.

FIG. 10 is a circuit diagram showing the circuit configuration of the amplifier 25 containing the integral circuit. As shown in FIG. 10, the amplifier 25 has the integral circuit composed of an operation amplifier in the front amplification stage and an output amplification circuit composed of an operation amplifier in the following amplification stage. The electric signals from the photomultiplier of the optoelectrical conversion element 24f are entered into an operational amplifier 25a which in turn constitutes the integral circuit, together with a condenser 25c and a switch 25d for controlling the integral operation. The output of the integral circuit is entered into an operational amplifier 25b and amplified with a gain to be determined by an external resistance, followed by transmission to an analog-digital converting circuit which follows.

Figure 11:
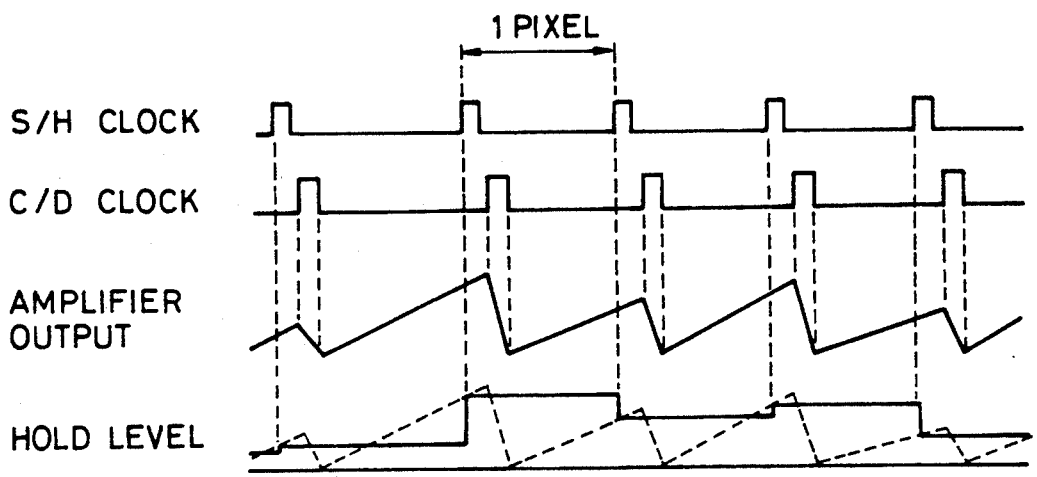
FIG. 11 is a time chart showing the timing of reading operations by the amplifier.

The operation in the amplifier 25 containing the integrating circuit having the configuration as described hereinabove will now be described with reference to the timing chart as shown in FIG. 11. The output of the photomultiplier of the optoelectrical conversion element 24f has a very large output impedance so that it can be regarded as if it is a source of electric currents. For the operational amplifier 25a, there is employed a high-input impedance of a FET (Field Effective Transistor) input type. Hence, when the switch 25d is turned off, the output current (suction current) ip of the photomultiplier (24f) flows entirely as it is through the condenser 25c. The output voltage of the operational amplifier 25a is converted into output in a lamp function type, as shown in FIG. 11. Such an integrating operation involves integrating for a period of time corresponding to one pixel, allowing a sampling circuit within the analog-digital conversion circuit 26 to sample signals so as to match with the timing of a S/H clock, and holding the resulting signals as they are. The integral output held is then supplied to an analog-digital converting circuit 26 which follows, and the analog signals are converted into digital signals.

After the signals have been held and the integral output has been supplied to the stage which follows, the C/D clock serving as a C/D control signal to be added to the switch 25d is made active, thereby discharging electric charges accumulated in the condenser 25c and returning the status to the initial status. The operations are repeated in the way as described hereinabove.

The amplification stage using the integrating circuit by the operational amplifier may be composed of a psudo-integrating circuit composed of a resistance and a condenser only. It is to be noted, however, that the integrating circuit by the operational amplifier having the configuration as described hereinabove can provide a higher signal-to-noise ratio because it can integrate the electric charges of the electric signals from the optoelectrical conversion element 24f to an almost complete level. Further, the integrating time can be changed in an arbitrary manner by changing the C/D clock of the C/D control signals for the switch 25d. Hence, a degree of amplification for amplifying faint signals in a comprehensive fashion can readily be adjusted. In this embodiment, the integral time can be controlled so as to agree with an area of the reading sample by corresponding to or synchronizing with the operation of the mirror driver 30 as shown in FIG. 4, thereby saving time for reading. Further, the speed of scanning the exciting light and the integrating time of the amplifier on the side of receiving light can be set so as to agree with the intensity of fluorescence from the sample with high freedom, thereby permitting a very flexible device configuration. In addition, when the integral operations are to be implemented with the condenser and the resistance only, the values of the condenser and the resistance can be shifted so as to become a time constant corresponding to the speed of scanning the irradiating light, so that the similar function can be realized.

The electric signals amplified by the amplifier 25 (FIG. 2) containing the integral circuit are entered into the analog-digital conversion circuit 26, where the analog signals are converted into digital signals. The signals indicative of the fluorescence detected, which are converted into digital data, are stored in the memory 28 and the data stored in the memory 28 is transmitted to the data processor 8 through an interface control circuit 29. The overall control for performing such a series of signal processing is carried out by the control circuit 27.

A description will now be made of the contents of the procedures for collecting and operating data by taking the case of reading the electrophoresis patterns of plural samples labelled with different fluorescent substances. The intensity of the fluorescence for each pixel is measured by vibrating the vibrating mirror 22 for each of inclination angles θ of the optical filter 24d. The value of the intensity of the fluorescence for each pixel has the relationship as shown in FIG. 12.

Figure 12:
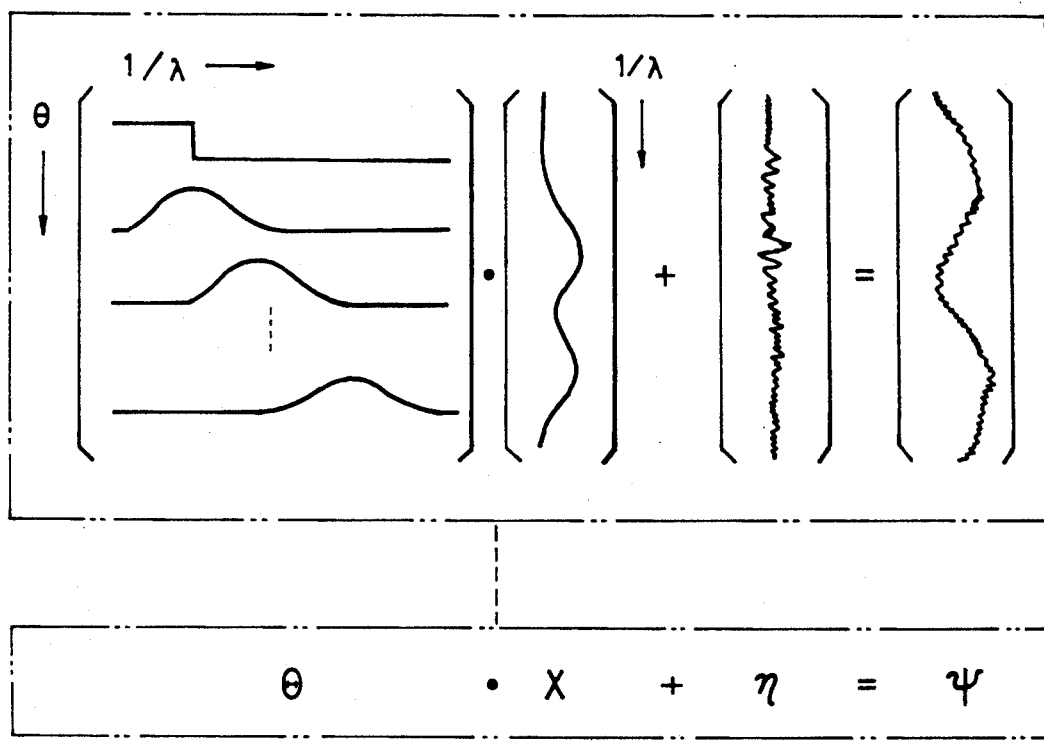
FIG. 12 is a schematic representation showing a typical sequence representing the relationship among the angle characteristic $\Theta$ of the optical filter 24d, the distribution X of the wavelengths of the fluorescent intensity at the pixels measured, the noise $\eta$ at the time of measurement, and the measured value $\Psi$.

FIG. 12 is a schematic representation showing the relationship of the electrophoresis patterns with the angular characteristic Θ of the optical filter 24d, the distribution X of wavelengths of the fluorescent intensity at the pixels measured, the noise η at the time of measurement, and the measured values Ψ. The value (measured value Ψ) of the intensity of fluorescence detected for each of the pixels is detected as the value in which the noise η is superimposed upon the intensity of the fluorescence because the fluorescent intensity X undergoes influences from the characteristic Θ of the optical filter 24d. Hence, the fluorescent intensity X is estimated by subjecting the measured values Ψ to inverse calculation by taking advantage of the method of least squares or the like.

The characteristic of the transmission wavelengths by the angles of the optical filter 24d is so set as to give the wavelength components that overlap partially with each other at the respective angles. When the fluorescent intensity of the fluorescent pigment to be used varies, the integral time of one pixel or the number of addition mean can be altered in a flexible manner in accordance with the fluorescent intensity for each of the angles at which the measurement is carried out, thereby providing image data with the high signal-to-noise ratio at a high speed. The resulting image has a value comparably approximate to the adjacent pixel due to diffusion at the time of electrophoresis or the like. By taking advantage of the characteristic of the detected image, the inverse calculation can be implemented at a high speed. This inverse calculation is executed by allowing a data processor of the control circuit 27 to fetch the measured data from the memory 28 and to implement the calculation on the basis of the predetermined program. The final data obtainable by the calculation within the memory 28 is transmitted to a data processor 8 through the interface control circuit 29. The control circuit 27 controls the overall signal processing. It is needless to say that data of the fluorescent intensity of each wavelength region can be obtained without operational processing by setting the pass bands of the optical filter 24d so as not to be superimposed upon each other at their respective angles. In this case, however, the intensity of the fluorescence to be detected is so faint that the highly sensitive optoelectrical conversion section is required.

A description will now be made of the method for reading the electrophoresis pattern by transcribing the electrophoresed sample onto a medium other than the gel medium by means of the multi-colored electrophoresis pattern reading system according to this embodiment of the present invention.

It is to be noted that this method is applicable particularly to the case in which it is difficult to label the sample in advance with a fluorescent pigment. The procedures of this reading method involves separating the sample, not labelled with a fluorescent pigment, on a gel member by means of electrophoresis, superimposing a thin film filter onto the gel member, and transcribing (sucking) the sample from the gel member by taking advantage of the same principle as the electrophoresis. As the thin film filter, there may be employed ones made of material such as nitrocellulose or nylon that in turn has been subjected to surface treatment so as to become likely to adsorb the sample. Thereafter, a substance (this substance being called "a probe") having the property likely to be connected to the sample transcribed onto the thin film filter is labelled with a fluorescent substance and then attached to the sample, followed by reading the pattern of the sample.

Figure 13:
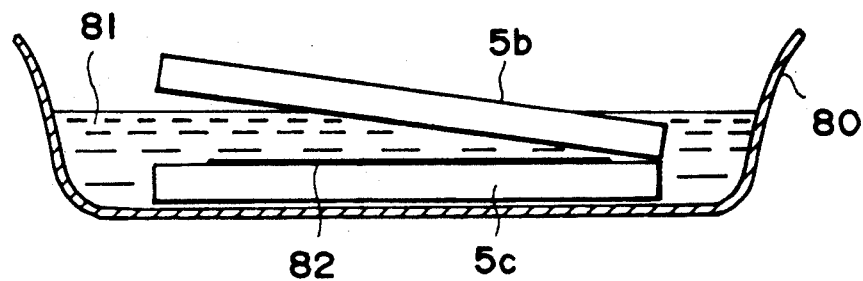
FIG. 13 is a schematic representation showing an example of the method for reading a sample labelled with a fluorescent probe and transcribed on a thin film.

FIG. 13 shows an example of the method for reading the sample transcribed onto the thin film filter and labelled with the fluorescent probe. Although the sample can be read directly by setting the thin film filter to the body of the instrumentation unit 7, the thin film filter is so white in itself and the scattered light is so strong that the sensitivity to detection of the fluorescence is lower by nearly one digit than the use of the gel member. Hence, in some cases, it may be difficult to read the sample having a weak intensity of fluorescence. A description will now be made of an example of a pre-processing method to be carried out to suppress the intensity of the scattered light to a low level. As shown in FIG. 13, the thin film filter 82 processed so as to emit fluorescence by transcribing the electrophoresed sample from the gel member and attaching the probe labelled with the fluorescent substance is immersed in a buffer solution 81 and then interposed between supporting plates such as glass plates 5b and 5c. In interposing the thin film filter 82 between the glass plates 5b and 5c, caution should be paid to cause no or little bubbles to be formed within a space between the glass plates. In this embodiment, glycerin is employed as the buffer solution 81, however, any substance may be employed as long as it has an optical refractive index as high as the thin film filter and the supporting plate and no adverse influence is exerted upon the thin film filter. As the thin film filter 82 has a large number of pores and the pores are closed or covered with the buffer solution 81, the level of the scattered light can be reduced to a great extent. After the thin film filter 82 has been interposed between the glass plates 5b and 5c, the sample transcribed upon the thin film filter 82 is read by means of the body of the instrumentation unit 7 in the same manner as the sample electrophoresed on the gel member is. In this case, the use of such a thin film filter as of a fluorescentless type allows the sample to be read with the highly enhanced signal-to-noise ratio.

Figure 14:
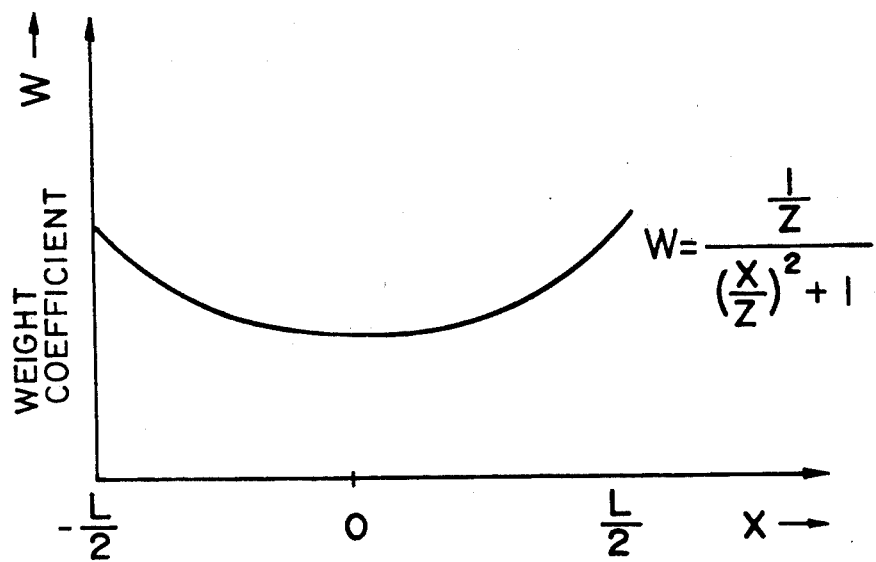
FIG. 14 is a schematic representation showing an example of correcting the scanning by signal processing by the optically scanning mechanism for scanning the mirror at equally angular speeds.

FIG. 14 is a graph for describing an example of implementing the scanning correction by the signal processing by means of the optically scanning mechanism for scanning the mirror at equally angular speeds. When the optically scanning mechanism used is composed of the vibrating mirror, as shown in FIG. 4, or a polygonal rotary mirror, there is no proportional relationship between the angular speed of rotating the mirror and the speed at which the surface of the electrophoresis section 5 is scanned, so that there may be a difference between the middle portion and the side portions of the surface of the electrophoresis section 5 in terms of the sensitivity to detection of the fluorescence to be detected from the sample of the electrophoresis section 5. For this reason, the optically scanning mechanism as shown in FIG. 4 has the mirror driver for driving the vibrating mirror equipped with a correction control circuit as shown in FIG. 6, thereby allowing the mirror driver for the vibrating mirror to correct the speed for driving the angular speed. Alternatively, the correction may be implemented at the stage of data processing for the electric signals of the fluorescence detected by correcting the characteristic for the sensitivity to detection of the fluorescence. In other words, in this case, the mirror is scanned at an equal speed (at an equally angular speed), and data on the intensity of the fluorescence read is corrected on the basis of a coefficient corresponding to the position X in which each fluorescence has been detected by taking advantage of the characteristic of the function having the relationship as an inverse function against the function of the speed at which spot lights moves, as shown in FIG. 14.

A description will then be made of a variant example of elements for structuring the multi-colored electrophoresis pattern reading system according to the embodiment of the present invention and of the configuration of an application example in which the multi-colored electrophoresis pattern reading system is employed as part of a system for determining a sequence of bases of a nucleic acid.

Figure 15:
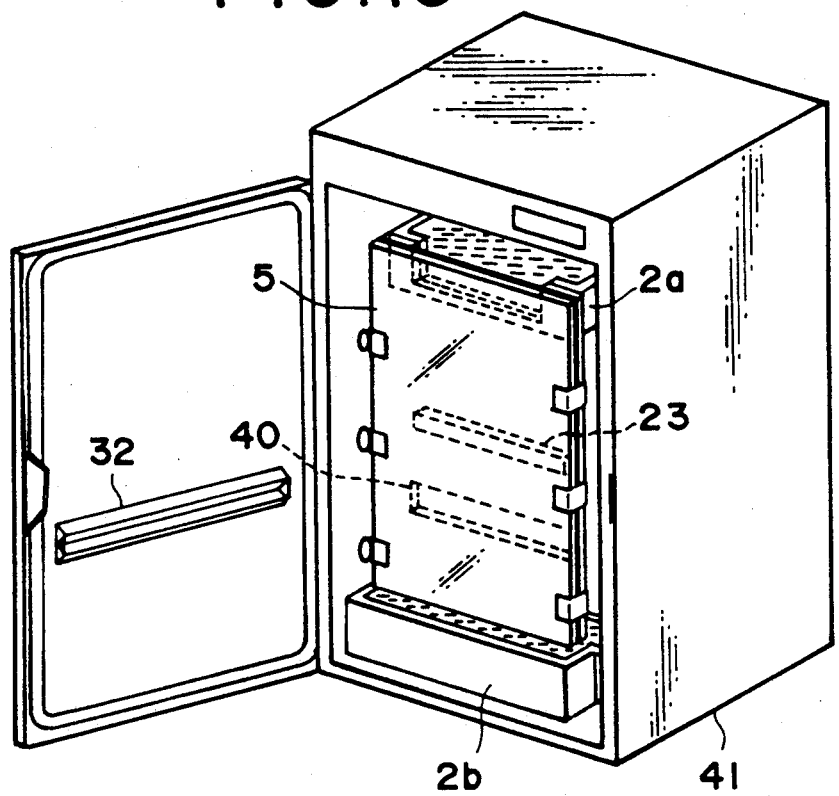
FIG. 15 is a perspective view describing the electrophoresis and reading unit for reading the patterns of electrophoresis as well as for implementing electrophoresis.

FIG. 15 is a perspective view showing the electrophoresis and reading unit for reading a pattern of electrophoresis as well as for implementing electrophoresis. As the gel member, there may be employed agarose gel or the like, and laser beams are irradiated in the direction of thickness of the gel member. As shown in FIG. 15, the electrophoresis pattern reading unit 41 comprises an electrophoresis unit 5 on the front side with respect to a door 41a and an instrumentation unit on the rear side of the door 41a. As the electrophoresis starts, the scanning light is radiated from the source for exciting light of the instrumentation unit into the electrophoresis unit 5 through an irradiating window 40. The light passed through the gel member of the electrophoresis unit 5 is trapped with the light trap 32 so as to cause no stray light to occur within the unit. The fluorescence emitting from the gel member in the electrophoresis unit 5 is collected after having been separated from the scattered light through the cylindrical lens 23, followed by implementing the processing in the same manner as the fluorescence of the pattern of electrophoresis is read by the reading unit.

Figure 16:
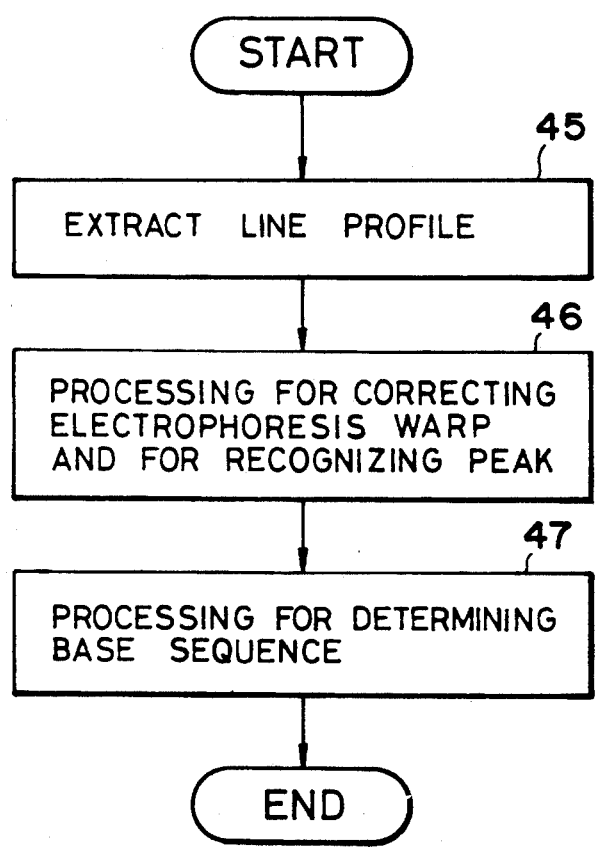
FIG. 16 is a flowchart showing the processing for determining the sequence of bases of a DNA fragment.
Figure 21A:
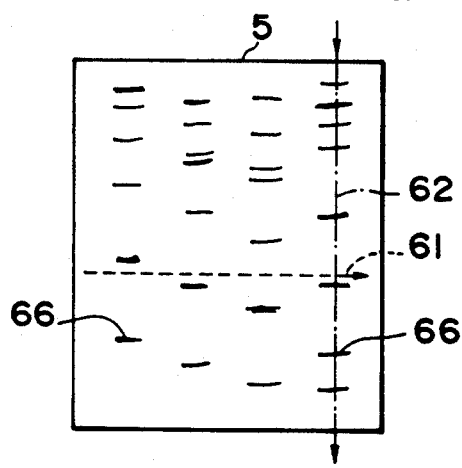
FIGS. 21a and 21b are schematic representations showing an example of pattern signals of fluorescent intensity of DNA fragments to be generated from the electrophoresis and instrumentation unit.
Figure 21B:
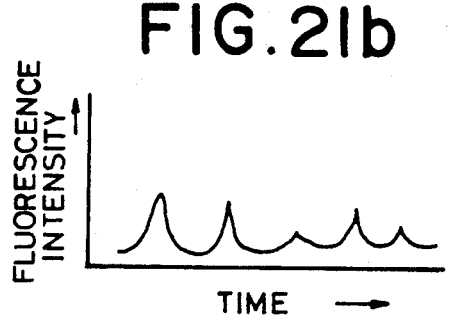
Figure 22:
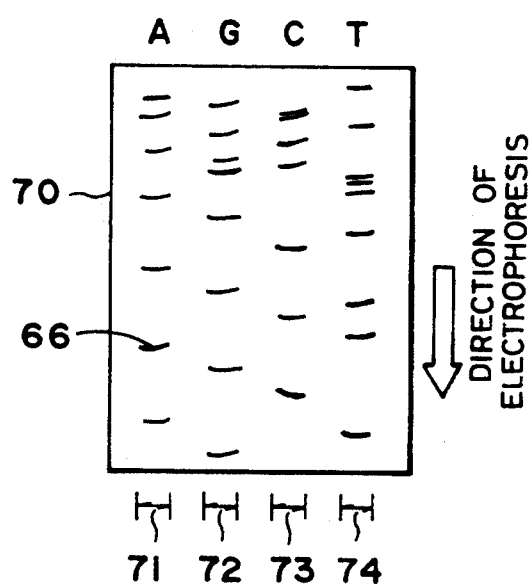
FIG. 22 is a schematic representation showing an example of distribution of DNA fragments electrophoresed.

FIG. 16 shows the flowchart showing the processing flow for determining the sequence of bases of the DNA. First, at step 45, processing for extracting a line profile is implemented. For example, as shown in FIG. 21(b), profile wave forms in proportion to the concentration of the fluorescence are extracted from lanes 71 to 74. The resulting profile wave forms are warped due to influences caused by various conditions of electrophoresis, including the irregular distribution of temperatures within the gel member 5a and a variation in the quality of gel itself. Thus, at step 46, processing for correcting a warp caused by electrophoresis is implemented, followed by processing for recognizing a peak of the wave form. The correction of the warp of the profile wave forms may be implemented, for example, by retracting or moving a factor of the warp, particularly relating to an distance of electrophoresis as data of time. The correction of the warp of the wave forms is implemented by taking advantage of the characteristics that the peak values of the lanes 71 to 74 for the bases A, C, G and T, respectively, do not overlap with each other if the samples of DNA fragments are identical. After the correction of the warp of the wave forms, the processing for recognizing the peak value of the line profile wave forms corrected is then implemented. In the processing at step 46, the processing for correcting the warp of the wave forms and for recognizing the peak values is repeated. The processing at step 46 is finished when the processing results satisfy appropriate conditions, such as a condition in which distances between the lanes for the bases A, C, G and T range within a desired scope.

Then, at step 47, the sequence of the bases is determined. The processing for determining the sequence of the bases of the DNA is implemented by arranging the symbols of the DNA of the lanes, to which the peak values of the lanes belong, from data of the positions of the peak values. In implementing the processing for determining the sequence of the bases from image data of the pattern of electrophoresis, all original data as the image data of the pattern of electrophoresis is automatically stored in a magnetic disk or other recording media so that the image data of the pattern of electrophoresis can be generated from the image printer in such a type similar to conventional autoradiography.

Figure 17:
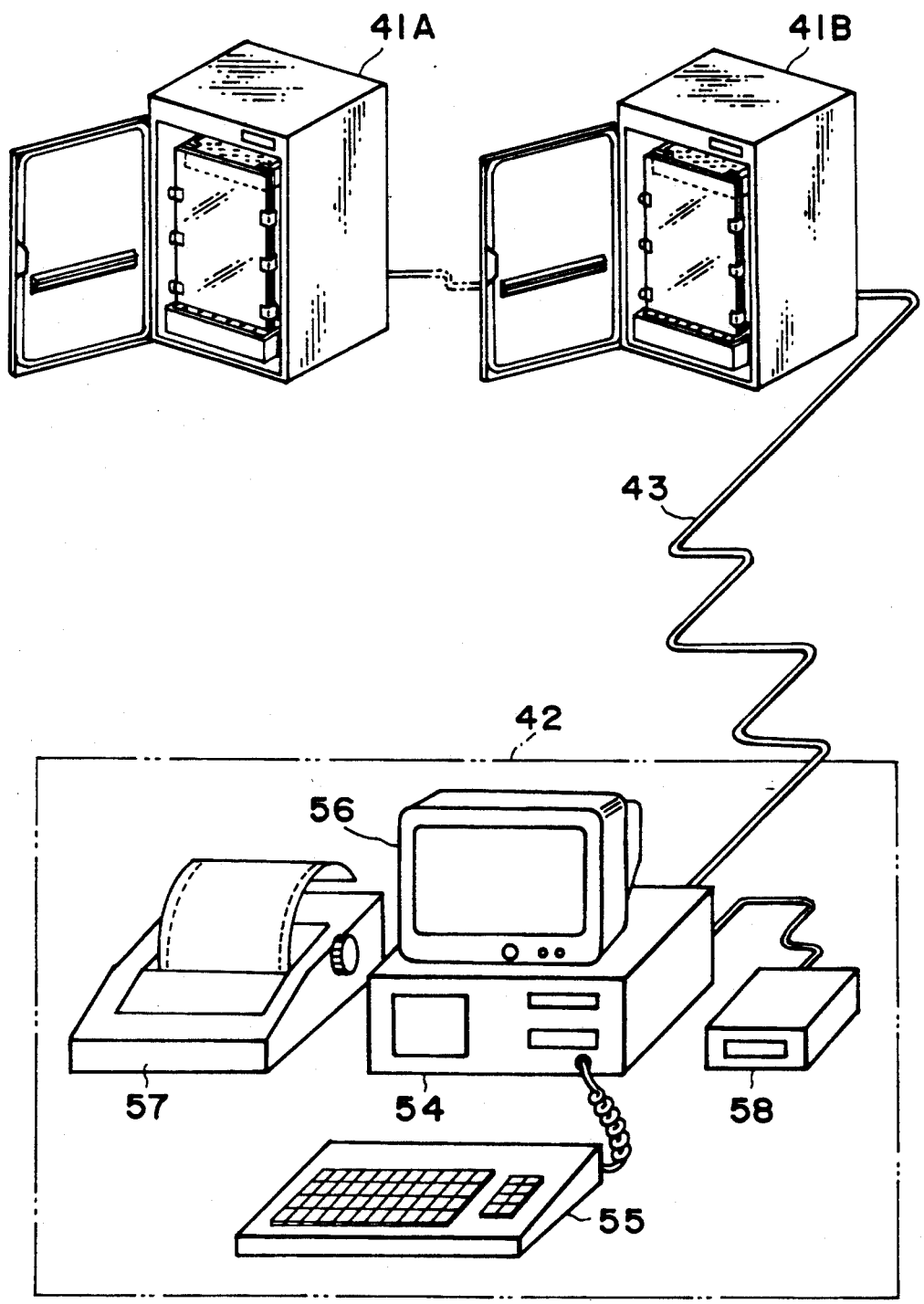
FIG. 17 is a schematic representation showing a system configuration in which a plurality of reading units of FIG. 15 are interconnected with each other.
Figure 18:
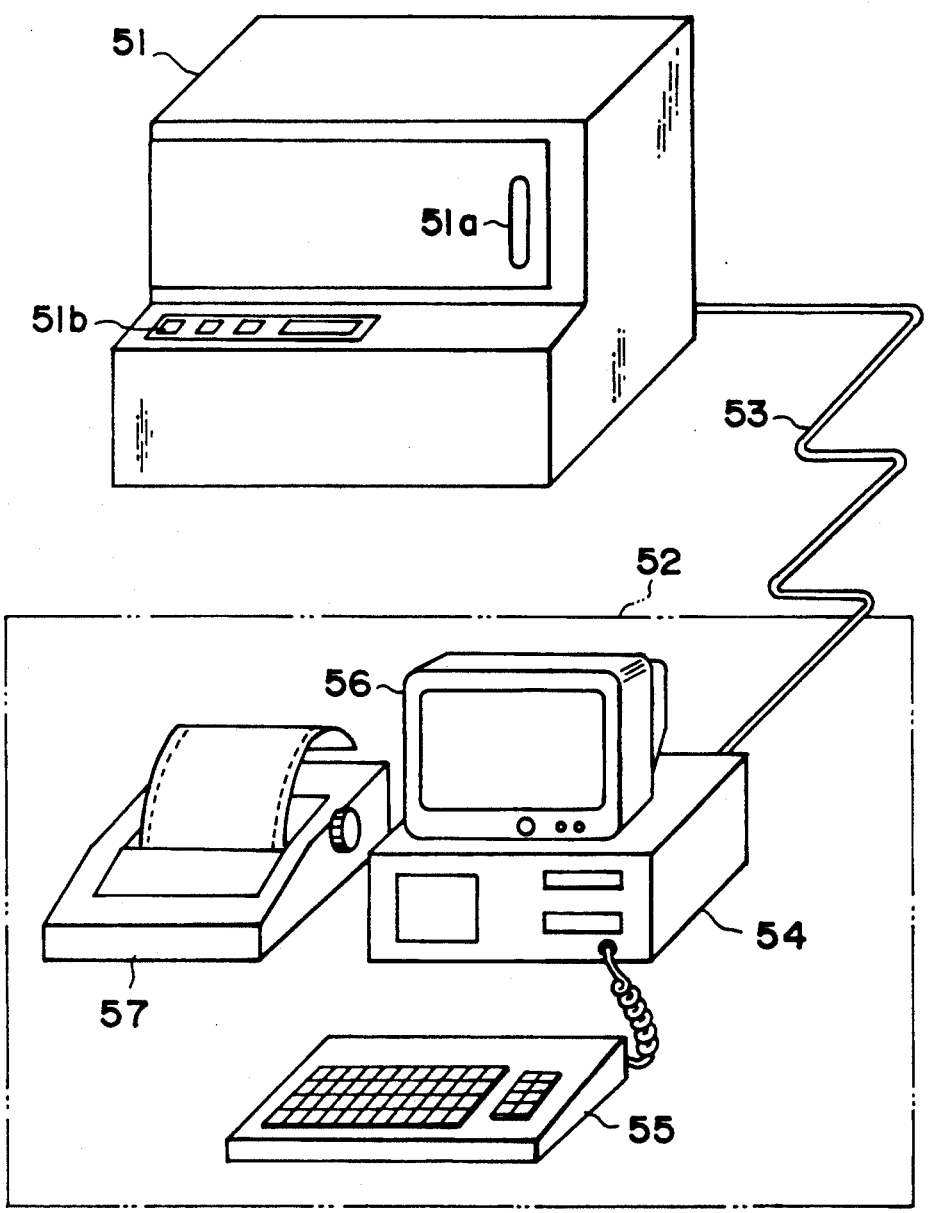
FIG. 18 is a perspective view showing an outlook of a conventional electrophoresis apparatus of a fluorescent type.
Figure 19:
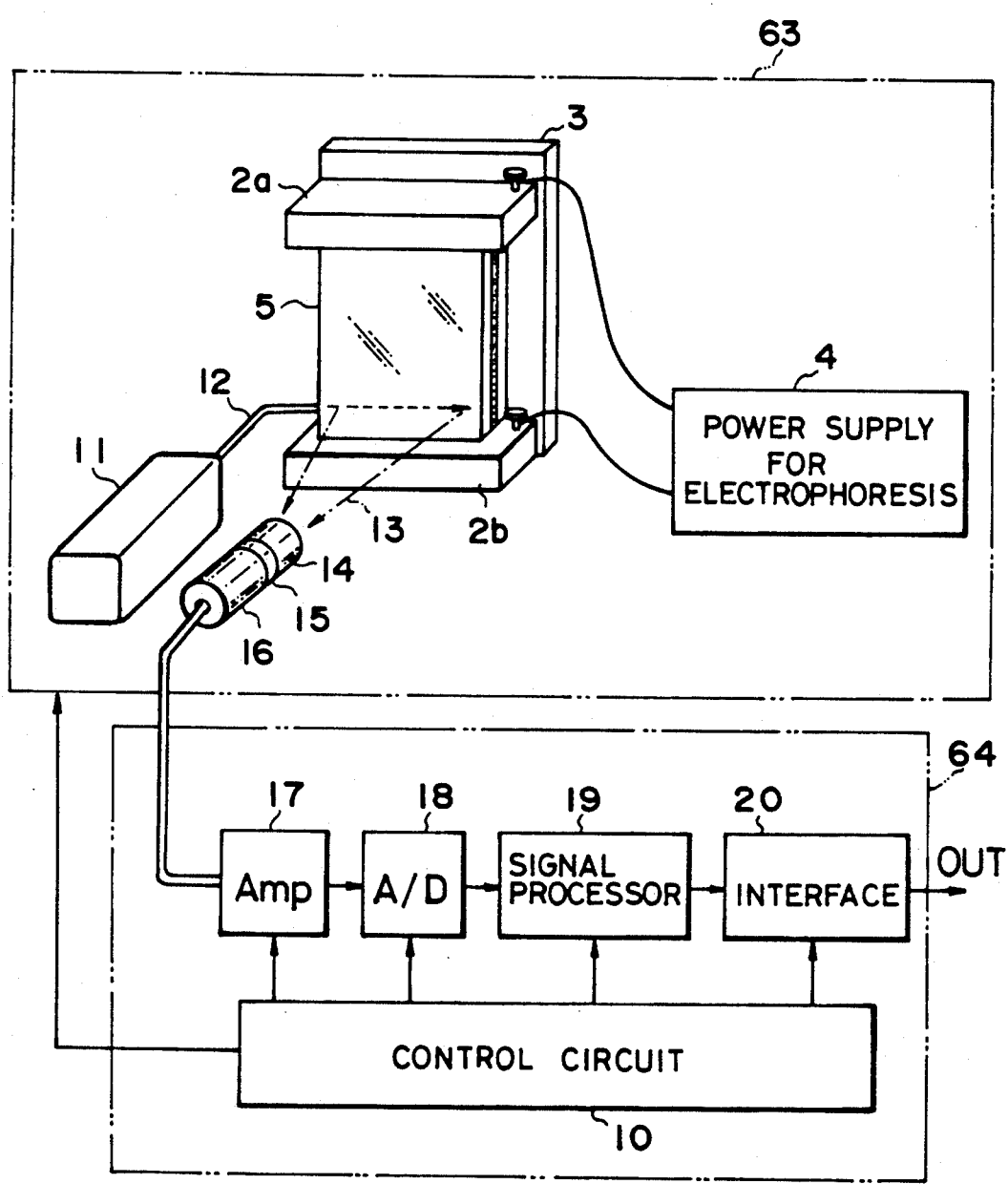
FIG. 19 is a block diagram showing the configuration of the inside of the electrophoresis and instrumentation unit of the conventional electrophoresis pattern reading apparatus.

FIG. 17 shows an example of the configuration of a system in which a plurality of the electrophoresis and reading units 41 are interconnected with each other. The electrophoresis and reading unit 41 capable of reading the pattern of electrophoresis concurrently with the implementation of electrophoresis requires a long period of time ranging from 5 to 8 hours for electrophoresis so that its throughput is less efficient. In order to improve this inefficiency, the system as shown in FIG. 18 is configured in such a manner that a plurality of units, such as the electrophoresis and reading units 41A and 41B, are interconnected with each other and all the electrophoresis and reading units 41A and 41B are to be operated concurrently. This system configuration serves as improvements in efficiency of electrophoresis and the reading of the pattern of electrophoresis. The plural electrophoresis and reading units 41 are interconnected with a data processor 42 through an interface 43 satisfying, for example, the specification of IEEE-488. As the data processor 42, the data processor 52 as shown in FIG. 18 may also be employed as it is. To the data processor 42 is interconnected a magneto-optical disk 58 having a large capacity so as to permit a large quantity of data of the pattern of electrophoresis read by the plural reading units 41A and 41B to be stored. As an interface capable of interconnecting the data processor with the electrophoresis and reading units 41A and 41B, there may be employed SCSI (Small Computer System Interface). In the system configuration as described above, each of the electrophoresis and reading units 41A and 41B is provided with a section capable of implementing the processing for operating data of each fluorescent wavelength. Alternatively, the data processor 42 may have a data processing section arranged so as to be employed independently or in common, thereby making the cost of the system configuration less expensive.

The resulting data of each fluorescent wavelength is recorded as image data on the magento-optical disk 58 having a large quantity of capacity. When the number of the patterns of electrophoresis to be read becomes large, the image data can be stored in a compressed form. As the technique for compressing the data, there may be employed a type of compressing data as causing no deterioration of quality of the image data even if compressed, by taking advantage of the characteristic of the image data of the patterns of electrophoresis In this embodiment, one pixel is constituted by two bytes and one line is constituted by 2,048 pixels. Further, the quantity of image data may exceed 20 Mb per one screen for one component of the fluorescent pigments, so that the quantity of the image data may outnumber approximately 100 Mb when four kinds of fluorescent pigments are employed. It is to be noted herein that, as the image of the patterns of electrophoresis has a relatively high correlation between the adjacent pixels due to a phenomenon of diffusion at the time of electrophoresis and for other reasons, the quantity of the image data can be compressed by taking advantage of this property. For instance, the quantity of the image data may be compressed to approximately one tenth as average by employing the data compression technique of such a type as recording simply the differential between the adjacent pixels and by compressing the data in a two-dimensional block unit. Further, as the electrophoresis has the characteristic that the pattern of electrophoresis is distributed in the form of a bell (a Gauss distribution) due to diffusion of the sample concurrently with migration of bands or dots constituted by aggregates of fragments having the same molecular weights and the distribution is so smooth, this characteristic may be utilized for efficiently compressing the image data. For example, the data may be recorded as a differential value obtainable by subtracting the value of a pixel from the value represented by the linear combination of the values of more than one pixel adjacent from each other. More particularly, the pixel positioned at the left end in each line is set as a standard and the differential value obtainable by subtracting the value of the pixel positioned next to the right from the value of the pixel positioned at the left end. Likewise, the differential values of the adjacent pixels are given and stored in this order. In addition, the technique of compressing data is also effective which is of such a type as giving an average of four pixels adjacent in four directions and storing the differential value from the average values. Such data compressing techniques require the relatively small number of steps for operation for compressing or expanding data and allow the compression or expansion of the data for a relatively short period of time. Further, it is possible to compress the data at a higher compression rate by implementing the compression of the data by means of various encoding methods such as arithmetic encoding methods or an autoregression model.

As described hereinabove, the multi-colored electrophoresis pattern reading system according to the embodiment of the present invention is high in flexibility because the electrophoresis plate (electrophoresis section) can be read after electrophoresis as it is in such a state that the electrophoresis plate is mounted. In addition, it is highly flexible due to the separate disposition of the reading section from the electrophoresis unit even if the reading of the results of two-dimensional electrophoresis would require a long period of time.

It is to be noted herein that the present invention is not understood to be restrictive in any respect to those embodiments or examples as described hereinabove and it is intended to encompass any variation and modification within the scope and spirit of the invention.

Further, as described hereinabove, the multi-colored electrophoresis pattern reading system according to the embodiment of the present invention can provide a structurally simplified system capable of reading the patterns of electrophoresis in multiple colors because the labels by plural kinds of different fluorescent pigments can be read concurrently and because the intensity of fluorescence in plural wavelengths can be measured at varying angles by taking advantage of the characteristic of the pass band wavelength of the optical filter at each of varying angles. Hence, the system can be configured at less expensive costs and with a high maintenance ability. Further, the results of electrophoresis obtained by implementing electrophoresis for two sample or more can be read concurrently by separating the components of fluorescence by the fluorescent wavelengths. In addition, the multi-colored electrophoresis pattern reading system of the present invention is so arranged as to cause a deviation such as a warp resulting from electrophoresis to occur on the samples in the same manner, so that the molecular weights of the two samples or more and other parameters can be compared, thereby making a comparison of the results of electrophoresis very simple and easy. In addition, the gel member is removed from the electrophoresis unit and mounted to the reading unit after the electrophoresis has been finished, so that the results obtainable by two-dimensional electrophoresis as well as by one-dimensional electrophoresis can be read in the same manner.

What is claimed is:

1. A multi-colored electrophoresis pattern reading system capable of labelling each of plural samples separately with each of plural fluorescent substances having a different fluorescence wavelength, subjecting the plural samples to electrophoresis to develop a pattern of electrophoresis, exciting the fluorescent substances labelled on the respective plural samples to emit fluorescence, and reading a fluorescent pattern emitting the fluorescence, comprising:

a light source means for irradiating the pattern of electrophoresis with irradiating light for exciting the fluorescent substance labelled on the sample to produce fluorescence;

a light scanning means for scanning the irradiating light while irradiating a gel in the direction of thickness of the gel with the irradiating light from the light source means;

a light receiving means for receiving the fluorescence separated from scattered light resulting form a reading surface on the basis of a position relationship of a light receiving path by setting a light receiving surface so as to be located in a direction different from an optical axis of the irradiating light;

a fluorescent-wavelength separating means for separating fluorescence having a predetermined wavelength from an optical signal received by the light receiving means, and having a separator and means capable of controlling an angle of incidence relative to an optical axis of the separator;

an optoelectric conversion means for generating electric signals by subjecting the optic signals passed through the fluorescent-wavelength separating means to optoelectrical conversion; and a signal processing means for subjecting the electric signals generated by the optoelectric conversion means to signal processing and converting the electric signals into a predetermined form of data representation.

2. A multi-colored electrophoresis pattern reading system as claimed in claim 1, wherein said signal processing means has:

an optical filter as the separator;

an integral circuit composed of a condenser and a switch for controlling an integral operation;

an integral circuit for controlling the integral operation in synchronization with a scan of irradiating light by said light scanning means; and means for changing an integral time and the number of scans for reading in accordance with the angle of incidence of the optical signals in the optical filter of said fluorescent-wavelength separating means.

3. A multi-colored electrophoresis pattern reading system as claimed in claim 1, wherein the fluorescent-wavelength separating means has a diffraction grating as the separator.

4. A multi-colored electrophoresis pattern reading system as claimed in claim 3, wherein said signal processing means has:
   an integral circuit composed of a condenser and a switch for controlling an integral operation;
   an integral circuit for controlling the integral operation in synchronization with a scan of irradiating light by said light scanning means; and
   means for changing an integral time and the number of scans for reading in accordance with the angle of incidence of the optical signals in the differential grating of said fluorescent-wavelength separating means.

5. A multi-colored electrophoresis pattern reading system as claimed in claim 1, wherein said signal processing means further comprises an image compressing means for compressing an image by giving a differential value obtainable by subtracting a value of a pixel positioned at a right side of each line from a value of a pixel positioned at the left side thereof, wherein image data read from the pattern of electrophoresis is stored as a compressed differential value.

6. A system of a multi-colored fluorescent type for determining a sequence of bases of a nucleic acid with a multi-colored electrophoresis pattern reading system as claimed in claim 1, further comprising:
   data processing means for deciding the sequence of the bases of the nucleic acid from image data of plural patterns of electrophoresis obtainable by the signal processing means; and
   wherein electrophoresis of plural samples is carried out and the sequence of the bases of the nucleic acid is determined from the plural patterns of electrophoresis.

7. A system of a multi-colored fluorescent type for determining a sequence of bases of a nucleic acid wherein a plurality of multi-colored electrophoresis pattern reading systems as claimed in claim 1 are disposed, each reading system comprising:
   a light source means for irradiating the pattern of electrophoresis with irradiating light for exciting the fluorescent substance labelled on the sample to produce fluorescence;
   a light scanning means for scanning the irradiating light and irradiating a gel in the direction of thickness of the gel with the irradiating light from the light source means;
   a light receiving means for receiving the fluorescence separated from scattered light resulting from a reading surface on the basis of a position relationship of a light receiving path by setting a light receiving surface so as to be located in a direction different from an optical axis of the irradiating light;
   a fluorescent-wavelength separating means for separating fluorescence having a predetermined wavelength from an optical signal received by the light receiving means with an optical filter capable of controlling an angle of incidence relative to an optical axis of the optical filter;
   an optoelectric conversion means for generating electric signals by subjecting the optic signals passed through the fluorescent-wavelength separating means to optoelectrical conversion;
   a signal processing means for subjecting the electric signals generated by the optoelectric conversion means to signal processing and converting the electric signals into a predetermined form of data representation;
   a data processing means for determining the sequence of the bases of the nucleic acid from the plural patterns of electrophoresis obtained by said signal processing means of each of the reading systems;
   wherein the plurality of the multi-colored electrophoresis pattern reading systems are operated concurrently with each other; and
   said data processing means of each of said reading systems reads the sequence of the bases of the nucleic acid from the plural patterns of electrophoresis obtained by said signal processing means of each of said reading systems.

* * * * *